(12) United States Patent
Stewart et al.

(10) Patent No.: US 11,974,835 B2
(45) Date of Patent: May 7, 2024

(54) SYSTEM AND METHOD FOR MEASURING PRESSURE WAVES IN DIALYSIS LINES

(71) Applicant: iTrend Medical Research Limited, Derby (GB)

(72) Inventors: Paul Stewart, Calver (GB); Jill Stewart, Calver (GB); Maarten Taal, Breedon on the Hill (GB); Nicholas Selby, Ashbourne (GB); Mohamed Tarek Eldehni, Dalbury Lees (GB); Venkata R Latha Gullapudi, Sheffield (GB)

(73) Assignee: iTrend Medical Research Limited (GB)

( * ) Notice: Subject to any disclaimer, the term of this patent is extended or adjusted under 35 U.S.C. 154(b) by 630 days.

(21) Appl. No.: 16/889,288

(22) Filed: Jun. 1, 2020

(65) Prior Publication Data

US 2020/0375471 A1  Dec. 3, 2020

Related U.S. Application Data

(60) Provisional application No. 62/855,069, filed on May 31, 2019.

(51) Int. Cl.
*A61B 5/022* (2006.01)
*A61B 5/00* (2006.01)
(Continued)

(52) U.S. Cl.
CPC .......... *A61B 5/022* (2013.01); *A61B 5/02141* (2013.01); *A61B 5/026* (2013.01);
(Continued)

(58) Field of Classification Search
None
See application file for complete search history.

(56) References Cited

U.S. PATENT DOCUMENTS

2011/0230772 A1*  9/2011  Koball ............... A61M 1/3656
604/4.01
2014/0246373 A1  9/2014  Kopperschmidt
(Continued)

FOREIGN PATENT DOCUMENTS

JP  2005261558 A *  5/2005  .............. A61M 1/14
JP  2005261558  9/2005
(Continued)

OTHER PUBLICATIONS

English machine Translation of JP 2005/261558, worldwide.espacenet.com, 22 pages, printed on Sep. 19, 2022 (Year: 2022).*
(Continued)

*Primary Examiner* — Matthew Kremer
*Assistant Examiner* — Matthew Eric Ogles
(74) *Attorney, Agent, or Firm* — Barnes & Thornburg LLP

(57) ABSTRACT

An aspect of the present disclosure describes an apparatus for non-invasive blood pressure monitoring that includes a plurality of pressure sensors, a plurality of sensor interfaces coupling the plurality of pressure sensors to at least one blood flow line disposed exterior from a patient, a pump for artificially generating blood flow through the at least one blood flow line, and a processor configured to receive pressure sensor measurements from the plurality of pressure sensors and generate a patient blood pressure estimation from the combined pressure sensor measurements.

19 Claims, 32 Drawing Sheets

(51) Int. Cl.
  *A61B 5/021* (2006.01)
  *A61B 5/026* (2006.01)
(52) U.S. Cl.
  CPC .......... *A61B 5/6866* (2013.01); *A61B 5/7257* (2013.01); *A61B 5/7267* (2013.01); *A61B 2562/0247* (2013.01)

(56) References Cited

U.S. PATENT DOCUMENTS

| | | |
|---|---|---|
| 2015/0045712 A1 | 2/2015 | Ninomiya et al. |
| 2015/0238676 A1 | 8/2015 | Giordano et al. |
| 2017/0326282 A1* | 11/2017 | Wilt .................... A61M 60/113 |
| 2018/0315182 A1* | 11/2018 | Rapaka ............. G06V 10/7747 |
| 2019/0000326 A1* | 1/2019 | Handler ............... A61B 5/7257 |
| 2019/0201609 A1* | 7/2019 | Ichikawa ............ A61M 1/3646 |
| 2019/0307337 A1* | 10/2019 | Little ................. A61B 5/02141 |
| 2020/0061281 A1* | 2/2020 | Desouza ............. A61M 1/1647 |

FOREIGN PATENT DOCUMENTS

| | | | | |
|---|---|---|---|---|
| JP | 2005261558 A | * | 9/2005 | |
| WO | WO-2018017623 A1 | * | 1/2018 | .............. A61M 1/14 |
| WO | WO-2018047956 A1 | * | 3/2018 | .............. A61M 1/14 |

OTHER PUBLICATIONS

English machine Translation of WO 2018/047956, Clarivate Analytics, 53 pages, printed on Sep. 19, 2022 (Year: 2022) (Year: 2022).*

Machine English Translation of Naoyuki, JP 2005/261558 A, worldwide. espacenet.com. 22 pages, printed on Sep. 19, 2022 (Year: 2005).*

International Search Report and Written Opinion issued to PCT/GB2020/051322 mailed Dec. 2, 2020, 18 pages.

International Preliminary Report on Patentability and Written Opinion issued to PCT/GB2020/051322 mailed Dec. 9, 2021, 9 pages.

* cited by examiner

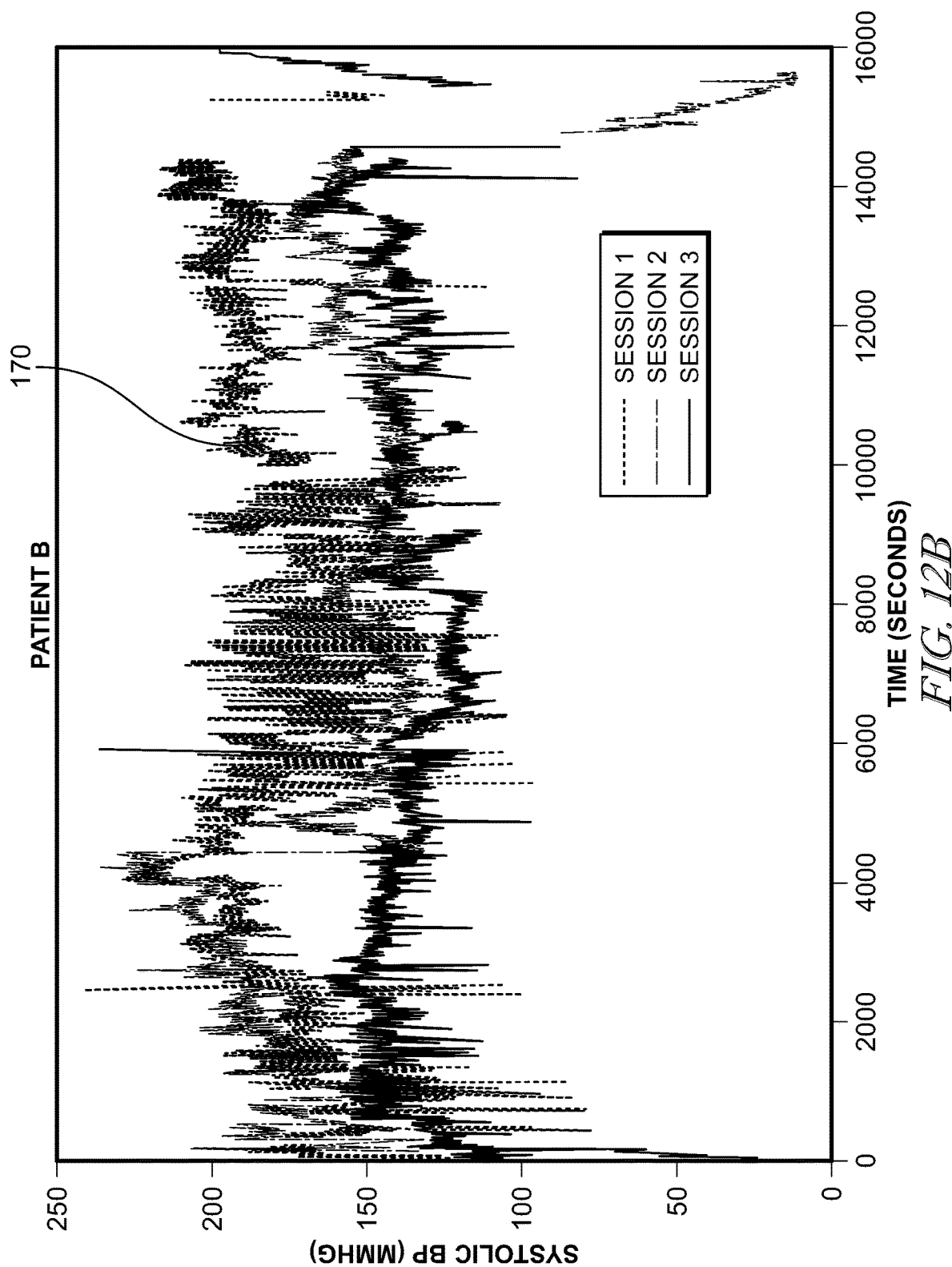

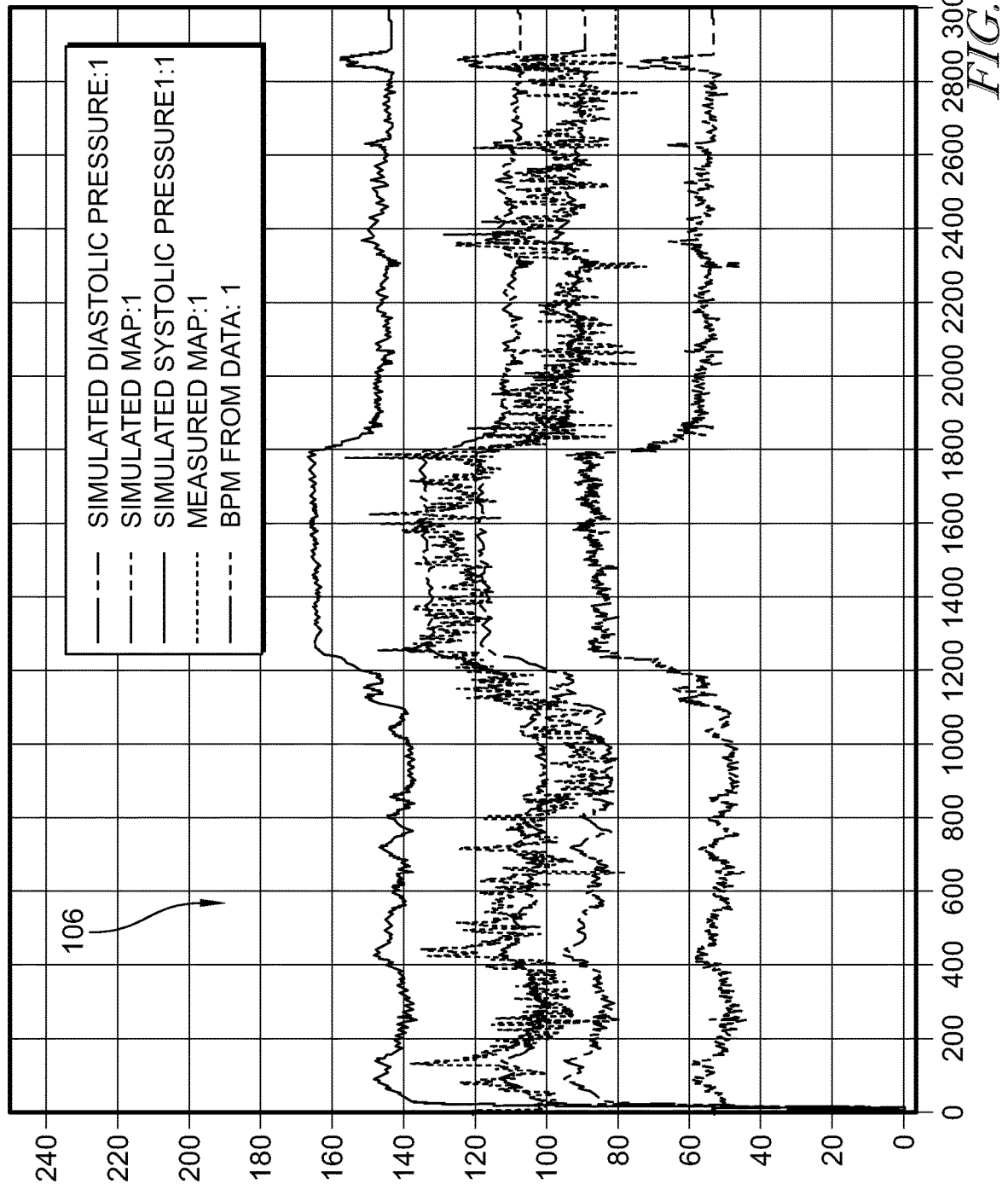

SYSTEM AND METHOD FOR MEASURING PRESSURE WAVES IN DIALYSIS LINES

CROSS-REFERENCE TO RELATED APPLICATIONS

This application claims the benefit of U.S. Provisional Patent Application No. 62/855,069, filed May 31, 2019, which is expressly incorporated by reference and made a part hereof.

TECHNICAL FIELD

The present subject matter relates to blood pressure observation, and more particularly, to analysis of blood pressure measurement with learning algorithms.

BACKGROUND

Intradialytic hypotension (critically low blood pressure experienced during treatment) remains a common and, often times, harmful complication of dialysis. Conventionally, arm-cuff blood pressure measurements are taken infrequently and do not facilitate reliable prediction of blood pressure-related events (e.g., hypotension). Continuous, non-invasive blood pressure measurement may allow the construction of models to predict hemodynamic instability, but current techniques for non-invasive blood pressure measurement are expensive, sensitive to patient movement/disturbances, and are relatively uncomfortable for patients during use. A comfortable, accurate, and robust non-invasive, continuous blood pressure monitor represents an improvement in the art. Further, processing and analysis of the data available from such an improved blood pressure monitor represents numerous improvements across an array of healthcare applications.

Patients receiving hemodialysis treatment for end-stage kidney disease (ESKR) are at a much higher risk of mortality due to cardiovascular disease. A key factor contributing to cardiovascular disease is intradialytic hypotension, a frequent complication affecting 15-50% of treatments and associated with subsequent vascular access thrombosis, inadequate dialysis dose, cardiac dysfunction, and mortality. The continuous monitoring of blood pressure during dialysis, particularly with respect to early detection and prediction of hypotension has the potential to significantly improve patient outcomes and may inform the choice of therapeutic intervention via modulation of dialysis time and/or duration, dialysate sodium concentration, and/or temperature on a per patient basis. Intradialytic hypotension (IDH) is a sudden event, and generally characterized by a decrease in systolic blood pressure greater than 20 mmHg or a decrease in mean arterial pressure by 10 mmHg. Associated symptoms can include dizziness or fainting, anxiety, muscle cramps, abdominal discomfort, nausea, and vomiting. In addition to the negative impact on patient well-being, IDH can result in truncated dialysis treatments and increase the risk for coronary and cerebral ischemic incidents. The ability to detect or predict impending IDH with sufficient time and accuracy to allow for mitigating action is the primary goal of developing a non-invasive continuous estimation of brachial blood pressure, as described in this disclosure.

Conventionally, arterial cannulation is regarded as the gold standard reference for continuous measurement of blood pressure. While a common procedure during high-risk surgery, arterial cannulation is not considered appropriate for hemodialysis patients where non-invasive monitoring is indicated. Instead, during hemodialysis, blood pressure monitoring is normally achieved via the use of an air-filled occluding arm cuff that provides a robust, but intermittent, measurement that disrupts the normal blood flow. Blood flow disruption caused by execution of an arm cuff blood pressure reading subsequently calls for a significant settling time before a next measurement may be taken.

Three other distinct methods for non-invasive monitoring of blood pressure have occasionally been used in research settings. First, arterial applanation tonometry involves a transducer positioned above a superficial artery compressing it against an underlying bone. Analysis of the resulting pulse wave has been extended to calculate systolic and diastolic pressure. This method has been used in cardiology and during anesthetized procedures to avoid the insertion of an arterial cannula. However, devices for performing arterial applanation tonometry are hand-held, operator dependent, and unsuitable for continuous monitoring. A second method for non-invasive continuous estimation of blood pressure is pulse transition time, which derives blood pressure estimations from measured photoplestimography (PPG) and electrocardiogram (ECG) signals during several cardiac cycles. Pulse transition time is then calculated as the time difference between the 'R' peak in the ECG signal and the corresponding time instance of an injection point on the maximum slope of the PPG signal. Pulse transition time may introduce inaccuracies in part because of unaccounted for physiological factors in the blood regulation mechanism and heavy reliance on accurate ECG triggering. A third alternative is the volume clamp (or vascular unloading) blood pressure monitoring method whereby an inflatable finger cuff is combined with an embedded photodiode to measure the diameter of the corresponding finger artery. Cuff pressure is adjusted to maintain a constant artery diameter, and the changes in cuff pressure are used to calculate a blood pressure curve in the brachial artery. Patients frequently report pain or discomfort at the fingertips where the finger cuffs are placed, and the finger cuff device can be unreliable in patients with reduced blood flow to the digits (e.g., dialysis patients, cardiac patients, diabetics). All three non-invasive methods are sensitive to patient movement (especially ECG signals) resulting in the placement of unacceptable and uncomfortable movement restrictions or restraints on patients during a four-hour dialysis treatment. Alternative non-invasive blood pressure monitoring methods may represent an improvement in the art.

The description provided in the background section should not be assumed to be prior art merely because it is mentioned in or associated with the background section. The background section may include information that describes one or more aspects of the subject technology.

SUMMARY

According to an aspect of this disclosure, an apparatus for non-invasive blood pressure monitoring is provided, comprising: a plurality of pressure sensors; a plurality of sensor interfaces coupling the plurality of pressure sensors to at least one blood flow line disposed exterior from a patient; a pump for artificially generating blood flow through the at least one blood flow line; and a processor configured to receive pressure sensor measurements from the plurality of pressure sensors and generate a patient blood pressure estimation from the combined pressure sensor measurements.

According to another aspect of this disclosure, a non-invasive blood pressure monitoring apparatus is provided, wherein the at least one blood flow line comprises an arterial line and a venous line, and wherein a pressure sensor is coupled to each blood flow line.

According to another aspect of this disclosure, a non-invasive blood pressure monitoring apparatus is provided, wherein the pressure sensor is coupled to the arterial line by a Y-connector.

According to another aspect of this disclosure, a non-invasive blood pressure monitoring apparatus is provided, further comprising an arterial line air trap and a venous line air trap, respectively, coupling the corresponding pressure sensors to each of the arterial line and the venous line.

According to another aspect of this disclosure, a non-invasive blood pressure monitoring apparatus is provided, wherein each air trap comprises an impermeable membrane and a filter.

According to another aspect of this disclosure, a non-invasive blood pressure monitoring apparatus is provided, wherein the processor is configured to receive an indication of a blood flow rate from the pump.

According to another aspect of this disclosure, a non-invasive blood pressure monitoring apparatus is provided, further comprising a learning algorithm executed by the processor to estimate a patient blood pressure from the pressure sensor measurements and the blood flow rate of the pump.

According to another aspect of this disclosure, a non-invasive blood pressure monitoring apparatus is provided, wherein the processor estimates the patient blood pressure over a period defined by a hemodialysis treatment session.

According to another aspect of this disclosure, a non-invasive blood pressure monitoring apparatus is provided, wherein the processor estimates the patient blood pressure over a period defined by a plurality of hemodialysis treatment sessions.

According to another aspect of this disclosure, a system for reconstructing blood pressure information is provided, comprising: a learning algorithm module; a plurality of pressure sensors disposed within arterial and venous dialysis lines; a flow rate sensor for measuring blood flow rate through a pump; a Fourier transform; and a processor and memory, wherein the processor applies the Fourier transform to line pressures observed from the plurality of pressure sensors; and wherein a decomposed function of the line pressures is combined with a measured blood flow rate to model a blood pressure.

According to another aspect of this disclosure, a system for reconstructing blood pressure information is provided, wherein the learning algorithm module learns physical dynamics of pressure waveforms in the arterial and venous dialysis lines.

According to another aspect of this disclosure, a system for reconstructing blood pressure information is provided, wherein the learning algorithm module models a relationship between pump speed and the pressure waveforms in the arterial and venous dialysis lines.

According to another aspect of this disclosure, a system for reconstructing blood pressure information is provided, wherein the learning algorithm module is trained on mean and amplitude data of the arterial and venous dialysis lines.

According to another aspect of this disclosure, a system for reconstructing blood pressure information is provided, wherein the learning algorithm module is trained on comparisons of the reconstructed blood pressure to a baseline blood pressure measured by a blood pressure cuff.

According to another aspect of this disclosure, a system for reconstructing blood pressure information is provided, wherein the learning algorithm module accounts for change in diameter of the arterial and venous dialysis lines and diameter of a pump dialysis line.

According to another aspect of this disclosure, a system for reconstructing blood pressure information is provided, wherein the learning algorithm module accounts for change in placement of the pressure sensors along the arterial and venous dialysis lines and the pump dialysis line.

According to another aspect of this disclosure, a method of generating blood pressure estimations is provided, comprising: connecting arterial and venous blood lines to a fistula disposed within a patient; arranging at least one pressure sensor to detect pulsatile pressure for each of the arterial and venous blood lines exterior to the fistula; coupling the arterial and venous blood lines to a peristaltic roller pump; accepting as inputs by a learning algorithm: arterial line pressure, venous line pressure, and pump speed; applying, by the learning algorithm, a Fourier transform to the inputs to generate an expected blood pressure of the patient.

According to another aspect of this disclosure, a method of generating blood pressure estimations is provided, further comprising: forming an arterial air trap; forming a venous air trap; and connecting the at least one pressure sensor for each of the arterial and venous lines to the corresponding air trap.

According to another aspect of this disclosure, a method of generating blood pressure estimations is provided, further comprising: inputting dimensions of the pump and blood lines to the learning algorithm.

According to another aspect of this disclosure, a method of generating blood pressure estimations is provided, further comprising: measuring baseline blood pressures for the patient with a blood pressure cuff; and training the learning algorithm by comparing generated expected blood pressures of the patient to the baseline blood pressures of the patient.

Other aspects and advantages of the present invention will become apparent upon consideration of the following detailed description and the attached drawings wherein like numerals designate like structures throughout the specification.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 12A and 12B compare systolic blood pressures observed for first and second patients during more than one dialysis session;

Figure 1A:
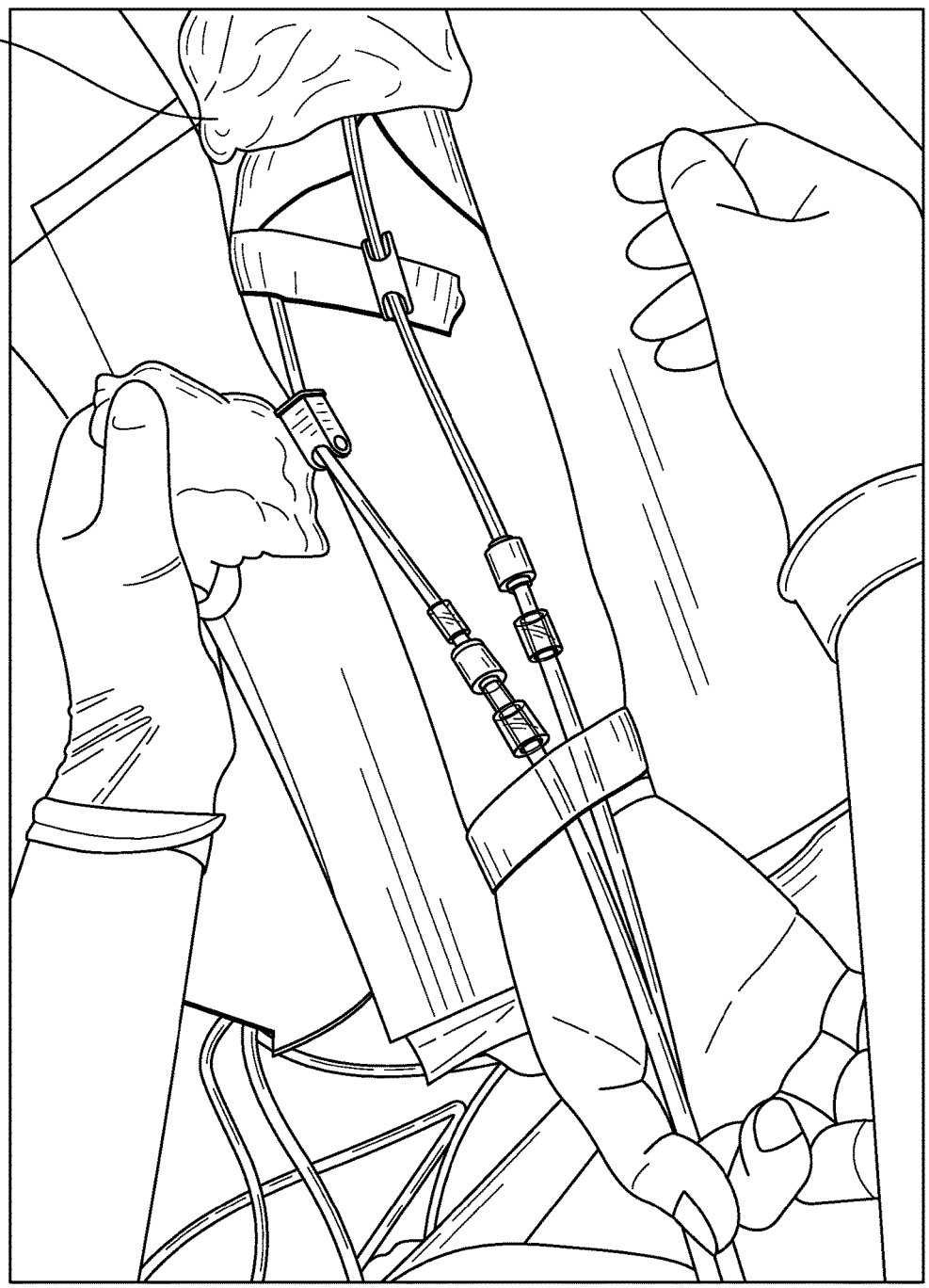
FIG. 1A illustrates a patient with a fistula receiving dialysis.
Figure 1B:
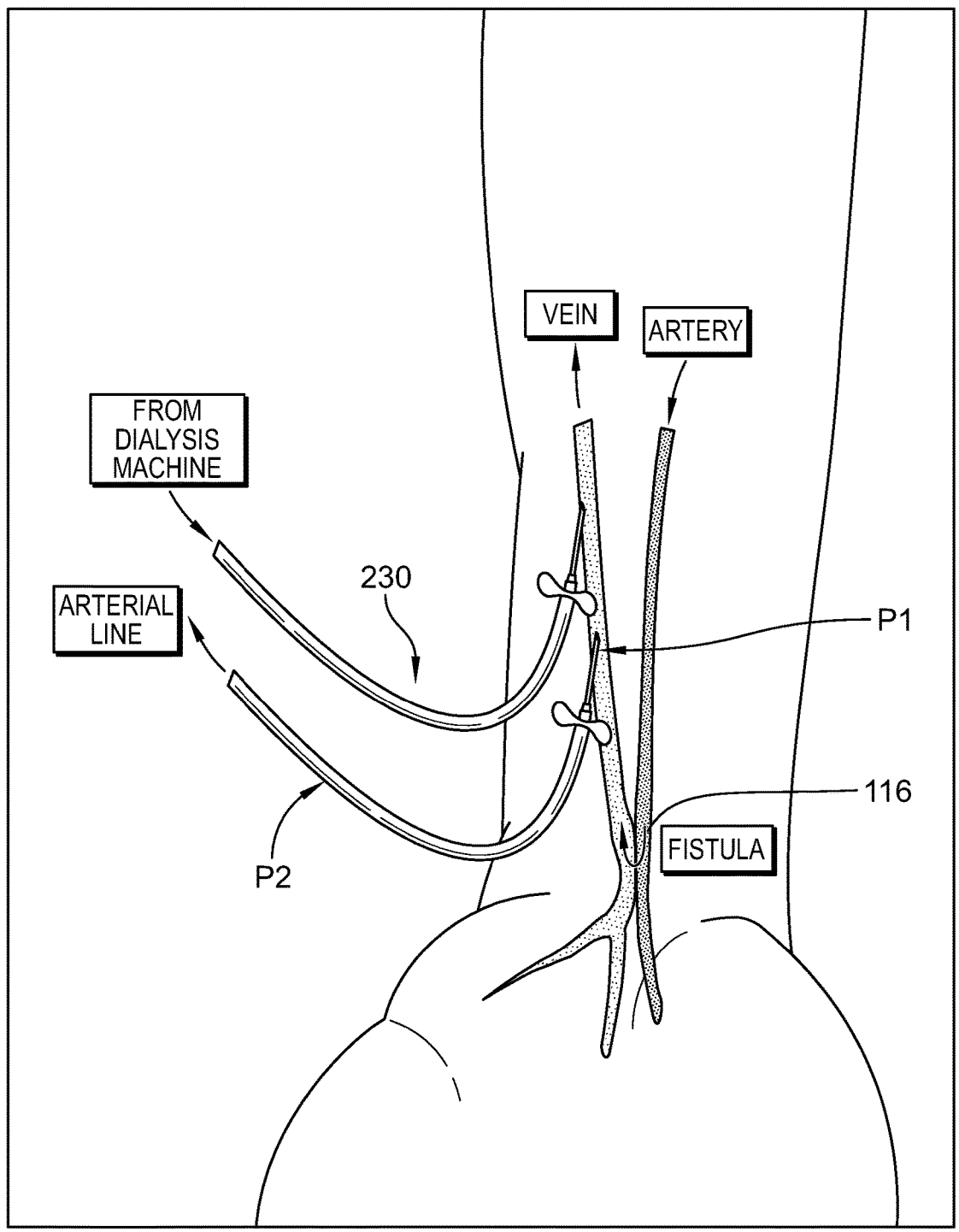
FIG. 1B illustrates a partially transparent patient with a fistula coupled to a vein and an artery for facilitating dialysis.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

I. General Overview

Generally, the present disclosure details, with reference to FIGS. 1-16, delivery of kidney haemodialysis patients with personalized treatment. According to the system and method, the personalized treatment will be optimized to limit and minimize the negative effects of dialysis and improve patient outcomes. The system and method for non-invasive blood pressure monitoring includes (i) a non-invasive, continuous, and highly accurate blood pressure measurement system/apparatus 102; (ii) an iterative learning algorithm/processing method 104 that derives estimated arterial blood pressure; (iii) a laboratory and/or software simulated cardiovascular system 106 that replicates arterial pressure waveforms using pre-recorded patient data or synthetic data; and (iv) a predictive algorithm/processing method 108 that generates a patient fingerprint and predicts patient outcomes.

The non-invasive blood pressure monitoring apparatus 102 is shown in and described with reference to FIGS. 1-6. One or more sensors coupled to dialysis lines may be used to reconstruct arterial blood pressure via an algorithm and analyze the reconstructed arterial blood pressure continuously. The apparatus 102 operates at a sufficient sampling rate and is suitably robust to withstand patient movements. The apparatus 102 may be tested by the laboratory cardiovascular experimental system 106 with one or more connections established within/along standard dialysis lines to a dialysis machine 200. Testing of the apparatus 102 with the laboratory cardiovascular experimental system 106 may be conducted with or without including pressure disturbances from a peristaltic blood pump 186 of the dialysis machine 200. The apparatus 102 detects accurate, robust, continuous blood pressure waveforms non-invasively from standard dialysis lines, which further contain pressure waveforms having significant disturbance components associated with the dialysis machine pump 186. The learning algorithms 104 and the predictive algorithms 108 develop a patient fingerprint and predict patient outcomes and/or group patients according to predictive features developed with artificial intelligence. Additionally, the simulated cardiovascular system replicates gathering of patient data and provides for additional adjustment and training of the learning algorithm 104 and the predictive algorithm 108.

A non-invasive blood pressure monitoring system and method derives relationships between a patient's brachial blood pressure and the pressures recorded within extracorporeal blood lines to and from the dialysis machine 200. Typically, two such blood lines are provided during hemodialysis. First, an arterial line that conducts blood from a patient to the dialysis machine 200. Second, a venous line that conducts blood from the dialysis machine 200 back to the same patient. Vascular access to the patient is provided by first and second large gauge needles (i.e. one needle connected on each of the arterial line and the venous line) inserted into a fistula. A fistula is a surgically enlarged blood vessel resulting from the connection of a vein onto an artery. Typically, a fistula is located within the non-dominant arm of a patient. As described hereinbelow with reference at least to FIGS. 2-6, pressure sensors may be placed into the extra-corporeal blood lines (Line A and Line V) in addition to, or in place of, pressure sensors disposed within the dialysis machine 200 and conventionally utilized for setup, calibration, and safety monitoring of the dialysis machine 200. This configuration, with pressure sensors disposed in the extra-corporeal blood lines, may facilitate a more robust and accurate approach to detection and derivation of continuous blood pressure signals from the arterial and venous lines.

II. Example Implementations

Apparatus and Method

The non-invasive blood pressure monitoring apparatus 102 includes one or more pressure sensors 112 with on-board signal amplification and linearization, e.g., industrial process control pressure sensors. The pressure sensor(s) 112 have been integrated with connectors that facilitate access to pulsating pressure waves detectable within injection ports of standard dialysis lines, e.g., by forming air traps proximal the first and second needles of the Line A and the Line V, respectively. Specifically with respect to FIGS. 1B-1D and FIG. 4, Line A designates the arterial blood line from a patient artery to the dialyzer 200, and Line V designates the venous blood line from the dialyzer 200 to a patient vein.

Typically, a fistula 116 is grafted into the arm of dialysis patients between an artery and a vein. Often, the fistula 116 (see FIGS. 1A and 1B) is placed at the wrist or along the inner part of the elbow depending on the size of the blood vessels present within the non-dominant arm of a patient. Hemodialysis is facilitated through the fistula 116 by placing two needles in different locations, attaching dialysis tubing thereto, and then connecting said tubing to the dialysis machine (i.e., an artificial kidney). Blood flows out of the fistula 116 through one needle to the artificial kidney and then back to the fistula 116 through another tube and needle.

Figure 1C:
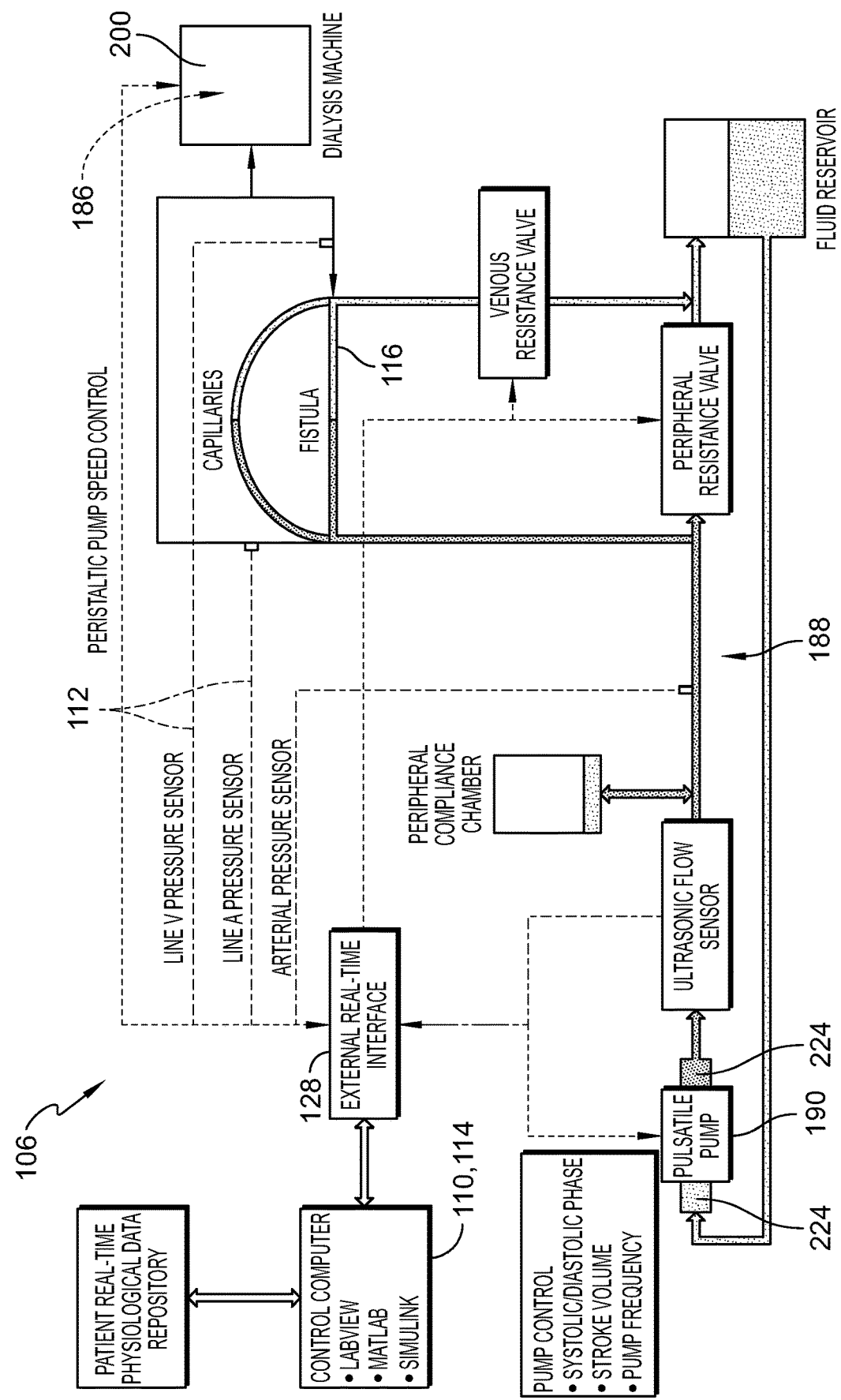
FIG. 1C diagrams a simulated cardiovascular system/apparatus.
Figure 1D:
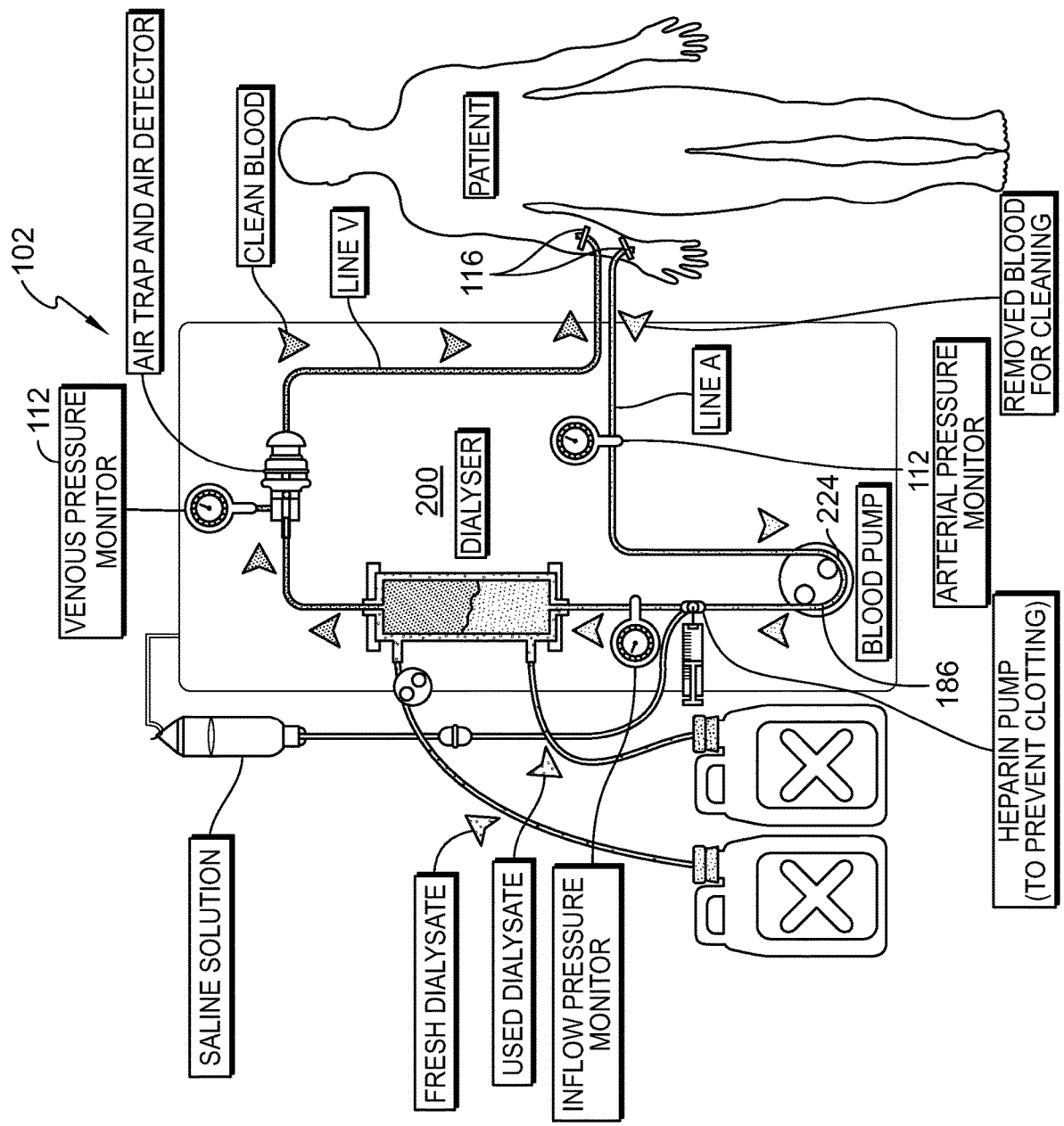
FIG. 1D diagrams a non-invasive blood pressure monitoring system/apparatus.
Figure 1E:
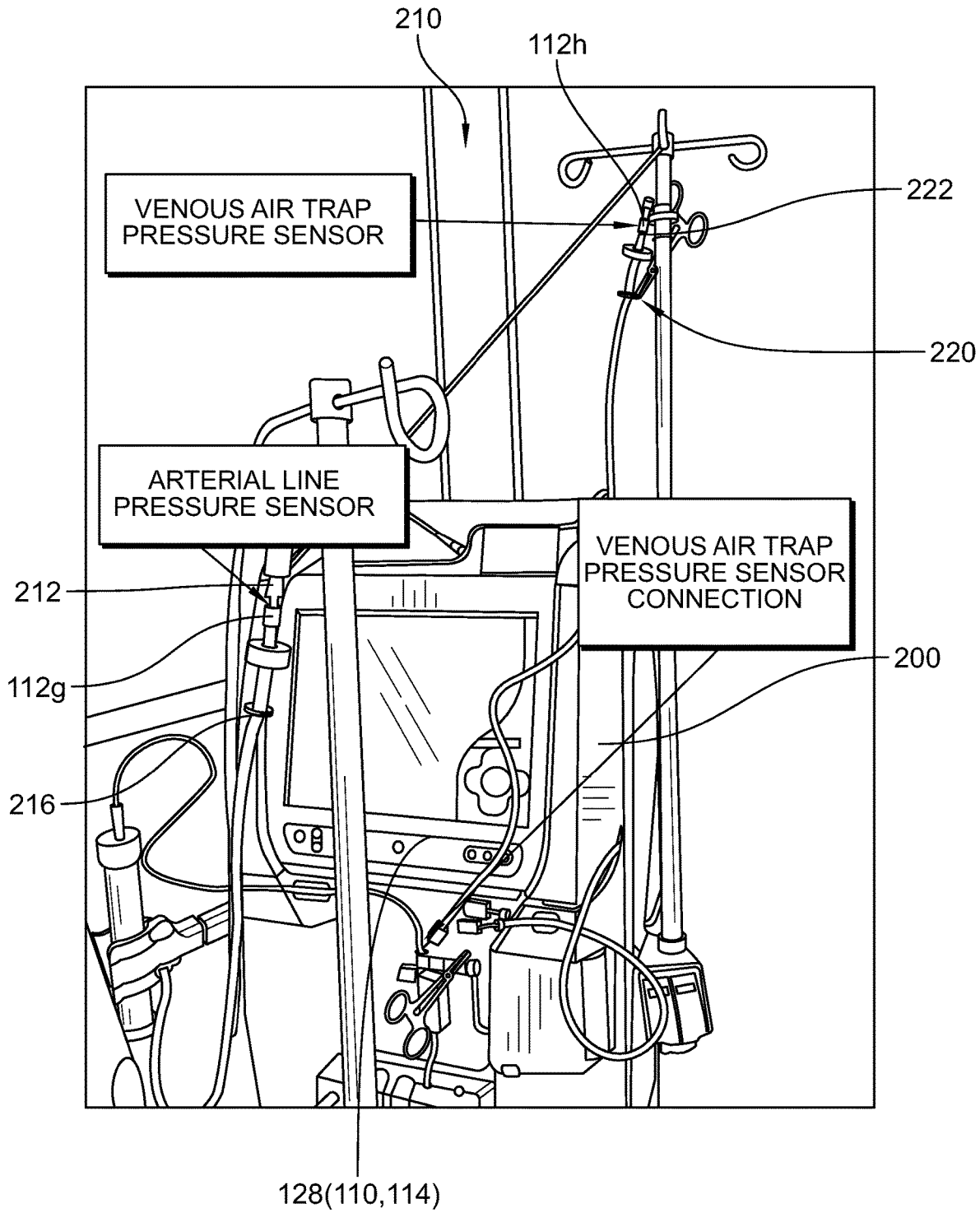
FIG. 1E depicts another embodiment of the non-invasive blood pressure monitoring system/apparatus of FIG. 1D.
Figure 6:
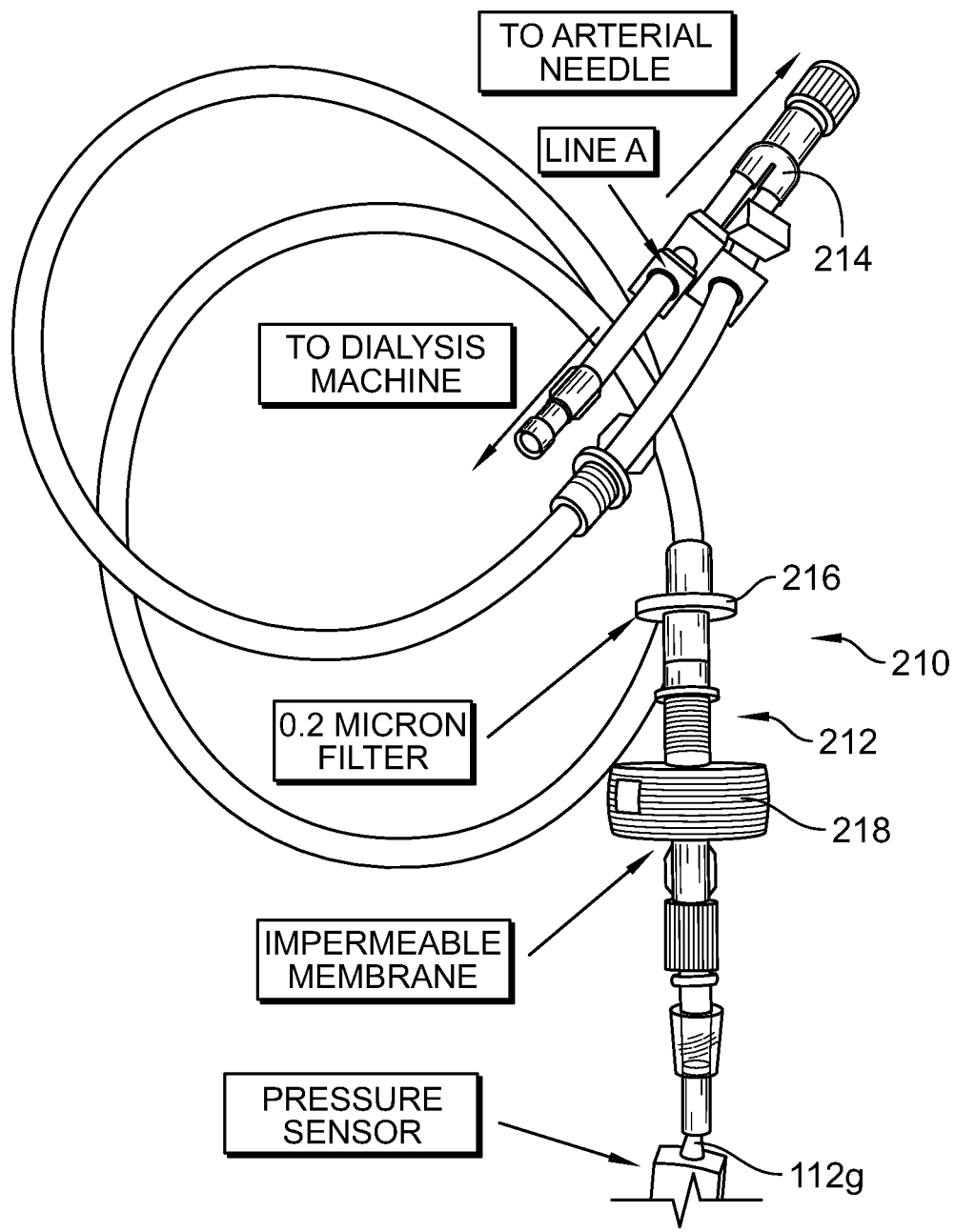
FIG. 6 is a fourth sensor interface for the non-invasive blood pressure monitoring system of FIG. 1D.

FIG. 1E is an example embodiment of the non-invasive blood pressure monitoring apparatus 102 including a fourth sensor interface arrangement 210 (see FIG. 6). The non-invasive blood pressure monitoring apparatus 102 comprises the fourth sensor interface arrangement 210 disposed along the extra-corporeal blood lines (Line A and Line V) and the dialyzer 200.

Figure 2:
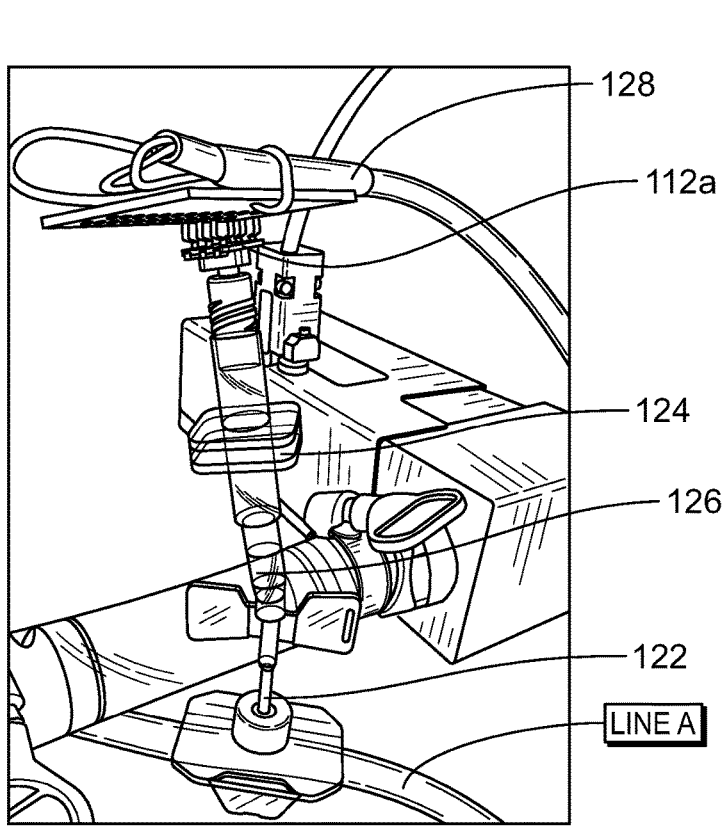
FIG. 2 depicts a first sensor interface for the non-invasive blood pressure monitoring system of FIG. 1D.
Figure 3:
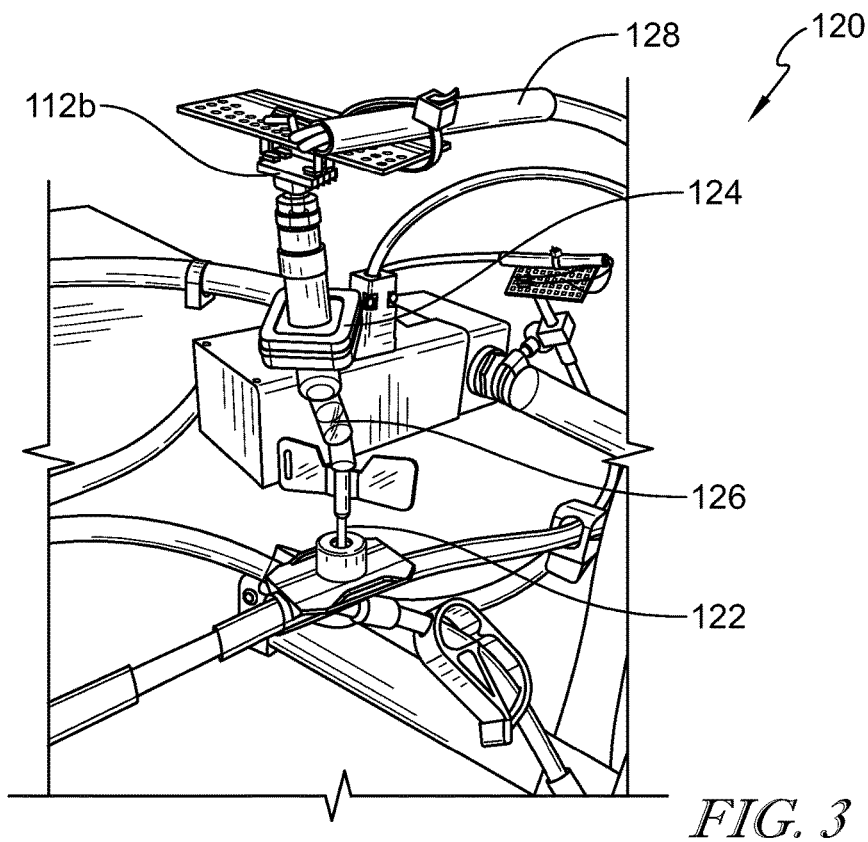
FIG. 3 depicts a second sensor interface for the non-invasive blood pressure monitoring system of FIG. 1D.

FIGS. 2-6 depict connection methods/apparatuses for interfacing the pressure sensor(s) 112 with the dialysis lines. A first example interface arrangement 120 is shown in FIGS. 2 and 3. As noted hereinabove, standardized dialysis lines have injection ports on Line A and Line V that facilitate injection of saline or drugs from a hypodermic syringe during treatment.

The first example interface arrangement 120 of FIG. 2 comprises a 14-gauge needle 122 inserted into the Line A injection port. The needle 122, on an opposite end thereof, is operatively connected to a diaphragm 124 via a small-bore tube 126. The diaphragm 124 is connected on the other side via another small-bore tube to the first compensated and amplified pressure sensor 112a (e.g., a Honeywell™ ABP series pressure sensor).

The pressure sensor(s) 112 are configured to continuously output a 0-5V analogue signal that is linearly proportional to a pulsating line pressure detected by the pressure sensor(s) 112. The pressure sensor(s) 112 are operatively connected to a data acquisition system 128 (e.g., a National Instruments™ (DAQ) multifunction device), which allows the incoming data to be captured, conditioned, and analyzed. The pressure sensors may establish two or more data acquisition channels communicatively coupling the pressure sensor(s) 112 to at least one processor 110 and memory 114 disposed in connection with the data acquisition system 128 or integrated therein. The function of the diaphragm 124 is to allow the pressure pulse waveforms to be freely transmitted to the sensor while preserving a sterile patient side of the device and preventing contamination of the pressure sensor(s) 112. FIG. 3 depicts another instance of the first interface arrangement 120 connecting a second pressure sensor 112b to the Line V injection port.

Figure 4:
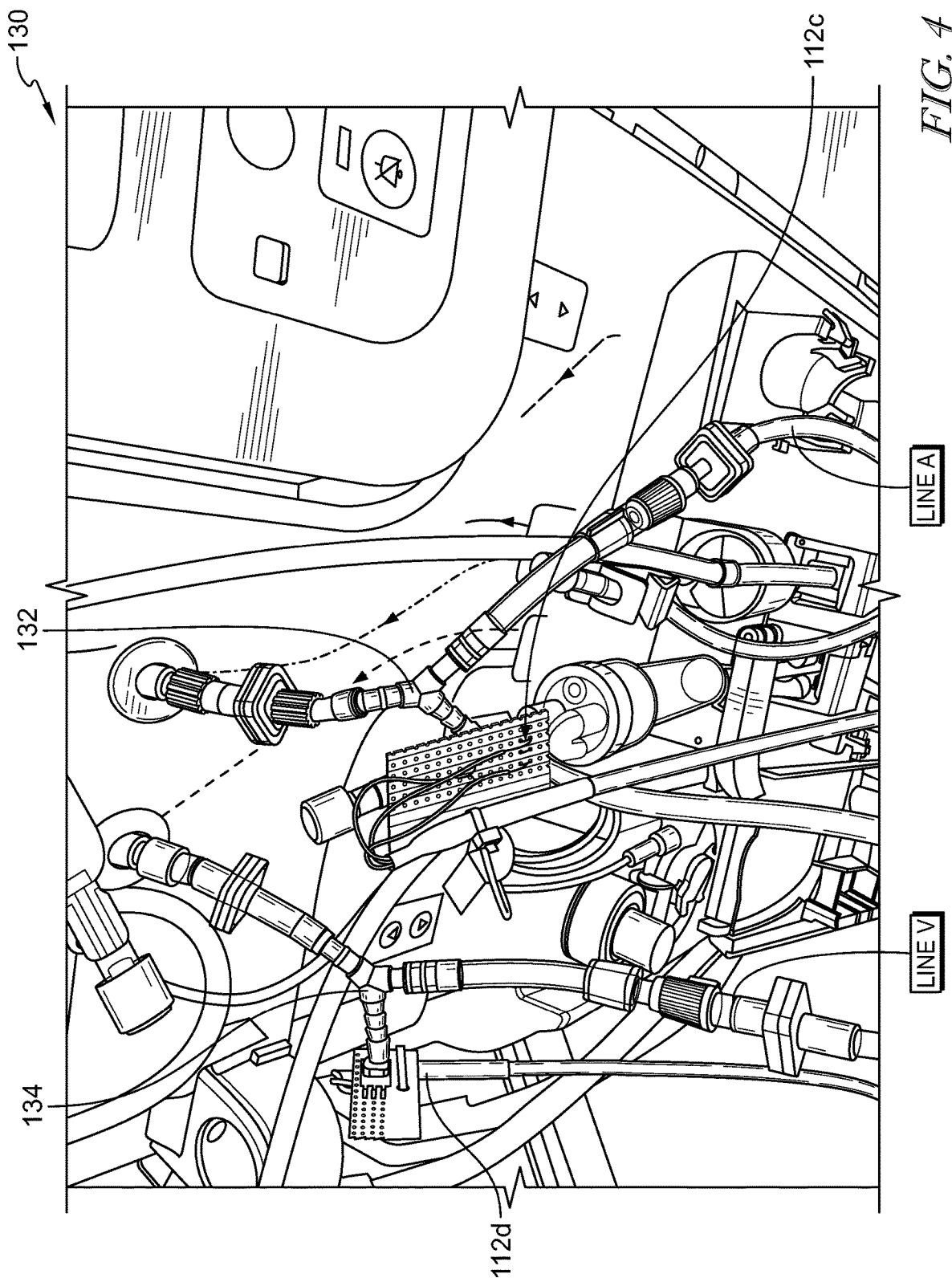
FIG. 4 depicts a third sensor interface for the non-invasive blood pressure monitoring system of FIG. 1D.

Referring now to FIG. 4 a second pressure sensor interface arrangement 130 is depicted. In the second interface arrangement 130, the first and second pressure sensor(s) 112c, d are respectively coupled to the Line A and the Line V via first and second t-pieces 132, 134 disposed on each of the lines at the dialyzer 200. The first and second t-pieces 132, 134 may be constructed from rigid plastic and are inserted into the lines to provide access for the pressure sensor(s) 112. Accordingly, the second interface arrangement 130 comprises insertion of the t-pieces 132, 134 and the pressure sensor(s) 112 into pressure monitoring take-off lines at the dialyzer 200 instead of at the patient side of the blood lines. In this arrangement, the dialysis pump (e.g., a peristaltic pump) is relatively close to the pressure sensor(s) 112 and may cause significant interference in the measured pulsating waveforms. As a result, estimation of the patient's blood pressure waveform in the presence of the pump interference may present unique challenges for processing algorithms.

Figure 5A:
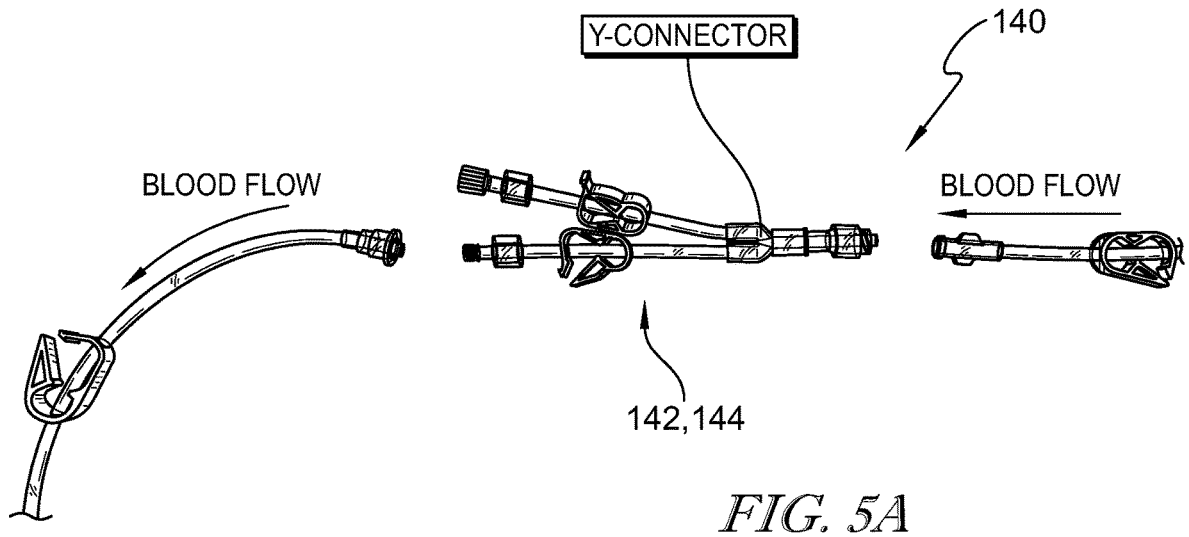
FIG. 5A is a disassembled view of the sensor interface of FIG. 4.

A third pressure sensor interface arrangement 140 is depicted in FIG. 5A in a disassembled view. The third interface arrangement 140 comprises first and second Y-connectors 142, 144 disposed proximal a patient end of the dialysis lines. Each of the Y-connectors 142, 144 is disposed between the fistula needle connector and the dialysis line on the respective arterial and venous lines (i.e., Line A and Line V). First and second pressure sensors 112e, 112f are connected to the first and second Y-connectors 142, 144, respectively, at each of the Line A and Line V.

Figure 5B:
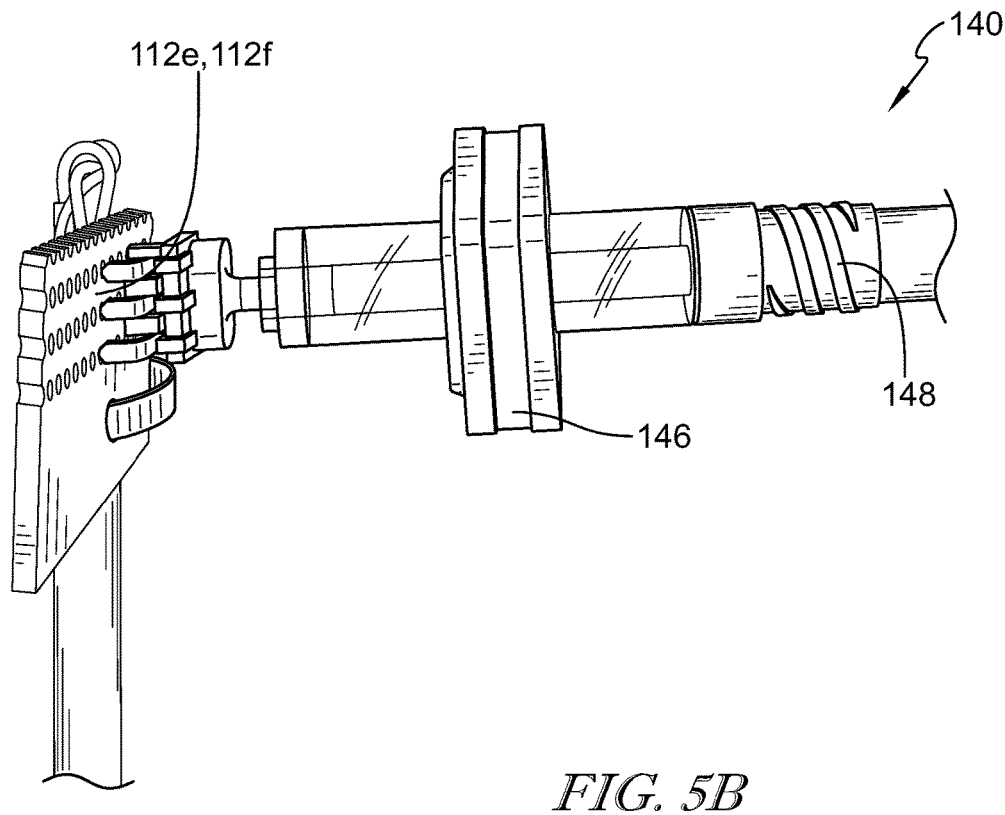
FIG. 5B is a partial, enlarged view of the sensor interface of FIG. 4.

Referring now to FIG. 5B, an enlarged view shows one of the pressure sensor(s) 112 of the third interface arrangement 140. In the third interface arrangement 140, a sterile diaphragm 146 has a threaded inlet 148 for attachment of the pressure sensor 112 to the Y-connector 142, 144. This arrangement optimizes the physical placement of the pressure sensor(s) 112 to the fistula 116 and, therefore, to the patient. The third interface arrangement 140 provides balanced measurement data as a result of the symmetrical layout thereof. The placement of the pressure sensor(s) 112 and the Y-connectors 142, 144 further exhibit increased mechanical robustness. The example shown in FIG. 6 is a fourth sensor interface arrangement 210 for the non-invasive blood pressure monitoring system 102. In FIG. 6, the example arrangement shows an air trap arterial line interface 212 comprising a Y-connector 214. A 0.2 micron filter 216, a membrane 218, and a pressure sensor 112g are disposed upstream from an arterial insertion needle within the arterial air trap 212 coupled to the Y-connector 214. The filter 216 forms a sterile barrier and operates to close completely if wetted by blood. This arrangement provides protection (from exposure to blood) for the sensor connections and the impermeable membrane. In the circumstance that a leak develops, or blood is otherwise introduced into the air trap arterial line interface 212, the filter 216 closes upon initial contact with blood to prevent blood from travelling further upstream.

The fourth sensor interface arrangement 210 further comprises an air trap venous line interface 220 (see FIG. 1E)

comprising another instance of the filter 216 attached directly to the venous air trap 222 and omitting a Y-connector. The venous blood line provides a 4 mm line connection point on the venous air trap interface 220 and a pressure sensor 112*h* operatively coupled to the venous air trap 222. In example embodiments, including the embodiment of FIG. 1E, the air trap venous line interface 220 is the final port on the venous side before return of blood to the patient. Additionally, the venous air trap pressure sensor 112*h* and the arterial line pressure sensor 112*g* are connected to the data acquisition system 128 (see FIGS. 2 and 3) via dedicated shielded cables, which include +5V and 0V power supplies to power the sensors from the data acquisition device 128. All data streams are time synchronised via a common real-time clock.

Figure 7A:
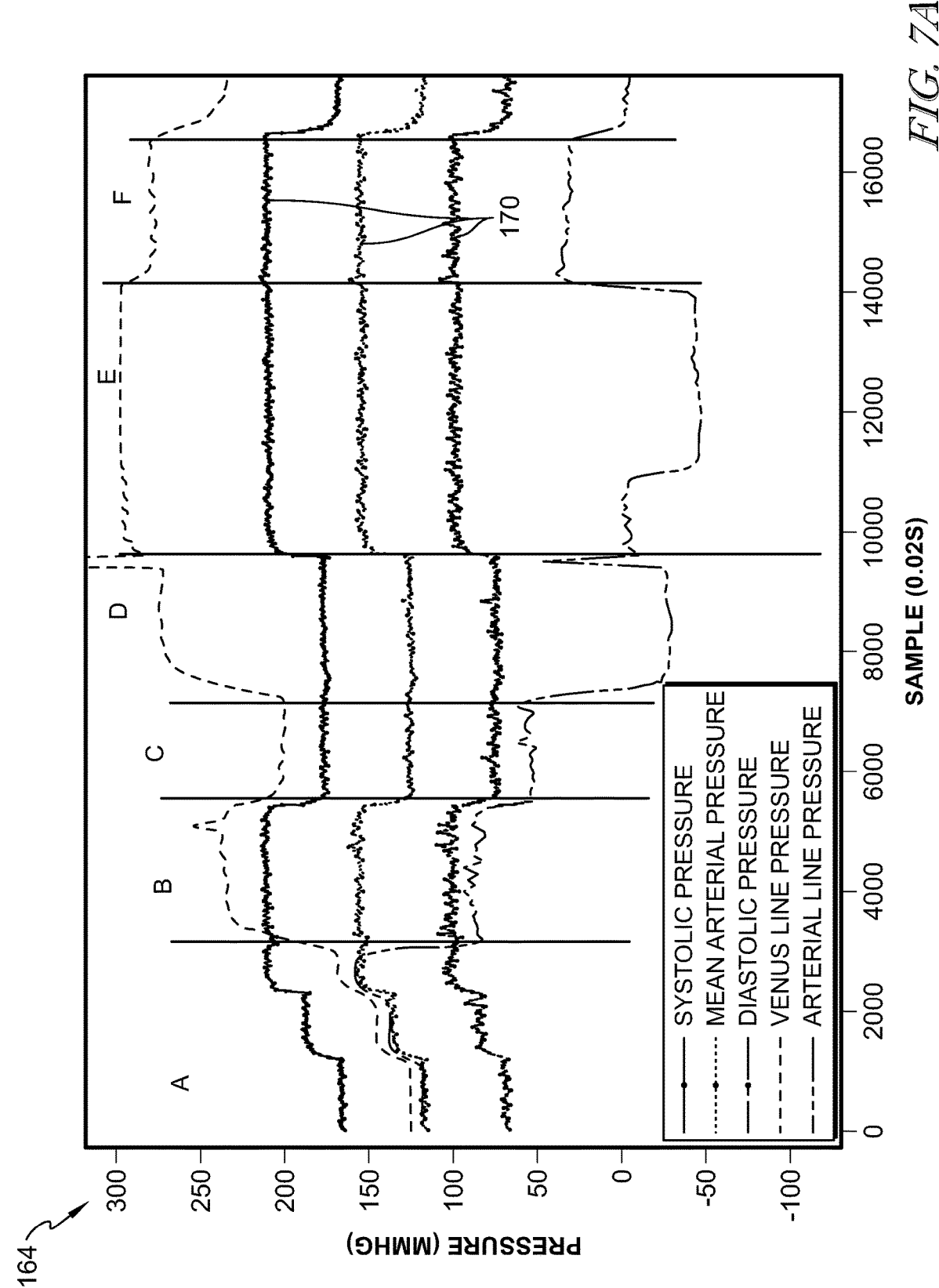
FIG. 7A charts hemodynamic data acquired by any of the systems/apparatuses of FIG. 1C, 1D, or 1E.

The apparatus 102 and associated algorithms operate with a number of different hemodialysis machines, dialysis lines, access needles, and/or other components, all having varying specifications. All of these variables alter the relationship between arterial pressure (i.e., blood pressure of the patient) and the pressure waveforms measured in the Arterial and Venous Lines (i.e., Line A and Line V), as shown in FIG. 7A. Additionally, the fistula 116 significantly affects the sensed blood pressure. Consequently, there is an element of adaptive learning necessary to fit the calculations to the effect of the wide parameter variations and a number of sub-algorithms to support those calculations.

Figure 7B:
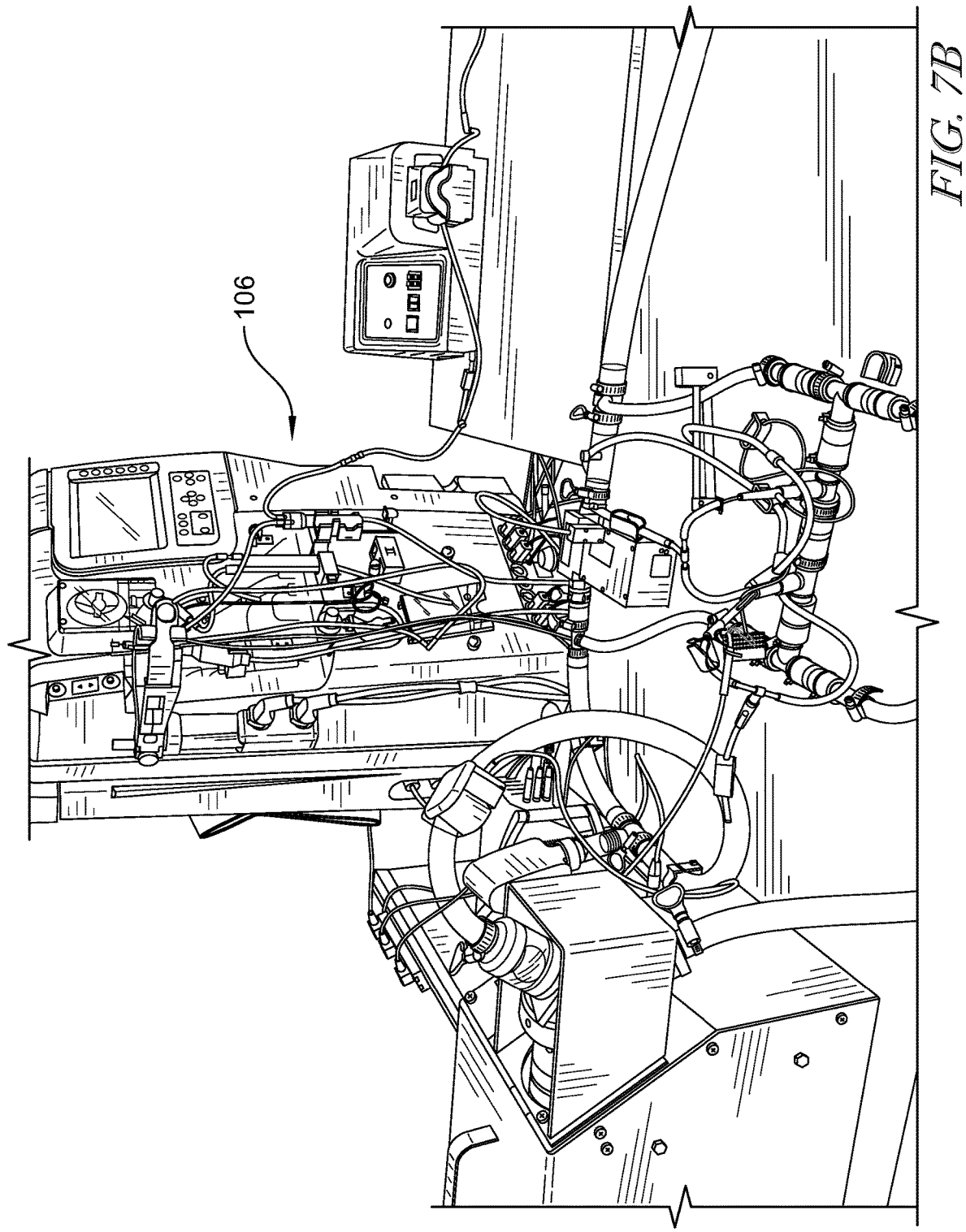
FIG. 7B depicts the simulated cardiovascular system/apparatus of FIG. 1C.

The measurement apparatus 102 may be connected to the laboratory simulated cardiovascular system 106, as shown in FIGS. 7B and 7C, which replicates arterial pressure waveforms using pre-recorded patient data or arbitrary 'synthetic' waveforms. Simulated arterial pressure in the cardiovascular simulator system 106 is available from a dedicated pressure sensor. The laboratory simulated cardiovascular system 106 facilitates the shaping of the blood pressure waveform (i.e., the pressure wave that travels out of the heart and down the Aorta into the arteries). A pulsatile blood pump 190 delivers fluid into a synthetic vascular system 188 (see FIG. 1C). The laboratory simulated cardiovascular system 106 provides a controllable heart rate, controllable stroke volume, controllable ratio between systolic and diastolic stroke, controllable peripheral resistance via a valve system, and controllable peripheral compliance via a bespoke air plenum chamber. The laboratory simulated cardiovascular system 106 further comprises a synthetic left arm constructed from tubing having a suitable diameter and compliance that branches from a main artery and returns to the venous low-pressure side of the apparatus. Additionally, the system 106 comprises a synthetic fistula in the arm bridging between artery and vein (i.e., high pressure and low-pressure sides of the apparatus) and allowing connection to a hemodialysis machine via appropriate venous and arterial lines.

Pressure and flow sensors are embedded at appropriate points in the laboratory simulated cardiovascular system 106. PC based real time data acquisition and control via one or more USB connections or other suitable connections enables the flow of incoming data and outgoing control commands to hardware of the laboratory simulated cardiovascular system 106. Control algorithms act on incoming data and user interface commands to calculate outgoing control signals. Similar to the measurement apparatus 102, the laboratory simulated cardiovascular system 106 comprises pressure sensors inserted into the arterial and venous lines.

Learning Algorithm and Predictive Algorithm

The blood pressure data adaptive learning algorithm and processing method 104 processes data collected by the apparatus 102 to develop an estimated/derived arterial blood pressure 150. The learning algorithm 104 and systems and methods for implementing same are described with reference to a number of examples including those illustrated in FIGS. 7A and 8-16. Experimentation and measurements may be conducted to collect pressure data 152 across a representative set of pressure waveforms developed at different and varying pump speeds. Once the pressure data 152 is gathered by the apparatus 102 as described hereinabove, the algorithm and/or process 104 utilizing artificial intelligence and/or machine learning techniques may be applied to the pressure data 152. Artificial intelligence embodied by the learning algorithm 104 may operate to learn the physical dynamics of pressure waveforms in the arterial and venous dialysis lines. Further, a Fourier series real-time filter 154 (referring ahead to FIG. 9B) is applied to the line pressure data 152 to reconstruct the arterial waveform 150 (See FIG. 7A) underlying the line pressure data 152 and associated with the patient/subject undergoing dialysis.

The present disclosure contemplates that the learning algorithm(s) 104, the pressure data acquisition apparatus 102, and the sensor interface(s) 120, 130, 140 may be integrated with an embedded microcontroller (e.g., Arduino) comprising one or more suitable processing modules and one or more memory modules (e.g., the processor 110 and the memory 114) for storing the pressure data 152 and/or the learning algorithm(s) 104. Also, in examples, one or more memory modules may instead be disposed remotely, such as in cloud storage and/or on a server, and accessible by the one or more processing modules through one or more wired and/or wireless connections. For example, the processor 110 and the memory 114 may be configured as part of the data acquisition system 128, the dialyzer 200, and/or as a separate control module. Also, example embodiments may integrate the data acquisition system 128, dialyzer control, and/or execution of the leaning algorithm(s) 104 as a single control module. Alternatively, these processing components may be separate, but communicatively coupled.

A blood flow rate through an extra-corporeal system 230 (i.e., the arterial line Line A, the venous line V, the dialyzer 200, and the pump 186) is important for analysis of the relationship between brachial and arterial line blood pressure measurements. A real-time measurement of blood flow facilitates estimation of blood pressure. During hemodialysis treatment, blood flow rate is often set when treatment begins and manually recorded for inclusion in medical records. For various clinical reasons, medical professionals may adjust the blood flow rate during hemodialysis treatment with or without recordation of such change in a medical record of the patient. In contrast, pressure waveforms measured by the pressure sensor 112*h* operatively coupled to the venous air trap 222 are dominated by the oscillations introduced by the lobes of the peristaltic blood pump 186. The periodic pressure waveform of pumps suitable for hemodialysis results from alternative compression and relaxation of a dialysis line 224, which is often 8 mm in diameter at the pump 186 (see FIGS. 1C and 1D), by the, typically, two lobes of the blood pump 186. As a result, the pump frequency may be derived from measurements of the real-time positive pressure sensor 112*h* disposed in the venous air trap 222 through the application of Fourier analysis. By this method, any reasonably well-behaved function may be expressed in terms of trigonometric or exponential functions. Considering a function $f(x)$ that is periodic on the interval $0 \leq x \leq L$, Fourier's theorem states that $f(x)$ may be written as the Fourier trigonometric series for the function as:

$$f(x) = a_0 \sum_{n=1}^{\infty} \left[ a_n \cos\left(\frac{2\pi n x}{L}\right) + b_n \sin\left(\frac{2\pi n x}{L}\right) \right] \qquad (1)$$

$2\pi$ is included in the arguments of the trigonometric functions; therefore, the n=1 terms have period L, the n=2 terms have period L/2, ... etc. for higher harmonics. For any integer n, an integral number of oscillations fit into the period L. In the instant application, the fundamental frequency of the blood pump 186 is desired; therefore, calculations may be made for n=1. The pump frequency is calculated and updated in real-time over a sliding window of data which is 5000 samples, or 5 seconds, wide. As the pump frequency is typically around 1 Hz, this ensures sufficient data, without including dynamics, thereby effectively generating a quasi-steady state measurement. Pump frequency is converted to flow in units of milliliters/sec by:

$$fl = \left( \left( \frac{fr(\text{rads}^{-1})}{2\pi} \right) \times 60 \right) \times (\pi r^2 Ln) \qquad (2)$$

In this example, fl is flow in milliliters/sec, fr is pump frequency in radians/sec, r is the radius of the dialysis line within the pump in millimeters and Ln is the effective length of line disposed within the pump in millimeters. Brachial pressure is regularly measured via inflatable blood pressure cuff, and data for all the sensors is synchronized and stored via the data acquisition device 128 (see FIGS. 2 and 3).

In example embodiments, it may be desirable to arrange the pressure sensor 112g on the arterial line as near as possible to the vascular access point on a patient. Pressure sensor placement is important because the access needle sits between positive pulsatile patient blood pressure at a patient end and blood-pump dominated negative pulsatile pressure at the other end (i.e., nearer the pump 186). Given that no suitable connector exists at an arterial needle end of the line, a Y-connector may provide access to both the dialysis line and the arterial line pressure sensor (see FIG. 6).

Modelling the relationship between arterial-line pressure and brachial pressure is extremely complex with significant physiological differences between patients. To produce a tractable model, a number of approximations may be performed. The brachial cuff measurement may effectively provide a quasi-steady state measurement single-instance sample of systolic and diastolic pressure. However, the brachial cuff measurement provides no dynamic information. Therefore, according to an example embodiment, the arterial line pressure may be filtered by a moving-average window over 5000 samples. Referring again to FIG. 1B, datum point P1 is defined as the tip of the arterial line needle, and pressure $P_1$ and area $A_1$ of below formula (3) are associated with point P1. Similarly, datum point P2 is defined as the location of the arterial pressure sensor 112g, and pressure $P_2$ and area $A_2$ are associated with it. It may be assumed that a steady (i.e., incompressible flow with negligible losses) blood flow rate may be expressed by Bernoulli and Continuity equations as:

$$J = A_2 \left[ \frac{2(P_1 - P_2)}{R\left(1 - \left(\frac{A_2}{A_1}\right)^2\right)} \right]^{\frac{1}{2}} \qquad (3)$$

Interpretation of this model, such as by a learning algorithm, may involve a number of assumptions. For example, horizontal flow and fully developed flow may be assumed at P1 and P2. Further, density and viscosity may be assumed constant over time. However, these assumptions may be unmeasurable and/or variable in practice from patient to patient, or may be time-varying during treatment. Additionally, the temporal and physical distance between the fistula needle site P1 and a measurement site at a brachial cuff (typically disposed on an opposite arm from the fistula 116) is significant (e.g., approximately 1 meter). Even for well-defined problems, theoretical flow $f$ is generally 2-40% lower than empirically measured flow due to the geometry and configuration of the non-invasive blood pressure monitoring apparatus 102. Therefore, formula (3) may be modified as:

$$J = A_2 \left[ \frac{2(P_1 - P_2)}{C} \right]^{\frac{1}{2}} \qquad (4)$$

In formula (4) C is an experimentally determined (or "lumped") cumulative parameter which approximates the unknown and/or unmodelled features of the non-invasive blood pressure monitoring system 102 and any unmet assumptions of the analysis. The cumulative parameter inherently accounts for the effect of different dialysis procedural details including, but not limited to: needle gauge size that may be used with different patients, blood pump flow rate according to different treatment prescriptions, and patient-specific parameters such as blood viscosity, blood density, and/or patient/blood temperature. Rearranging formula (4) for C results in:

$$C = \frac{2(P_1 - P_2)}{\left(\frac{f}{A_2}\right)^2} \qquad (5)$$

The expression of formula (5) allows computation of C from measured values. When $P_2$ represents measured arterial line pressure, and if the cumulative parameter coefficient C includes the relationship developed between $P_1$ and measured brachial pressure $P_b$, then a quasi-linear relationship between arterial line pressure and brachial pressure can be derived from equation (5). However, if the variable C is accurately modelled and time-invariant then the quasi-linear relationship predicts or reconstructs brachial pressure without measurement thereof. The relationship is given by:

$$-P_2 = 03\left(\frac{F}{A_2}\right)^2 C - P_2 \qquad (6)$$

where C defines a gradient of the relationship between measured $P_2$ and $P_b$. As a result, C may be used as a predictor of estimated $P_b$ based on measured $P_2$. Given the expectation that C will contain time varying and unmodelled terms, it can be predicted that there will be variation around the mean for individual patient measurements.

Figure 8A:
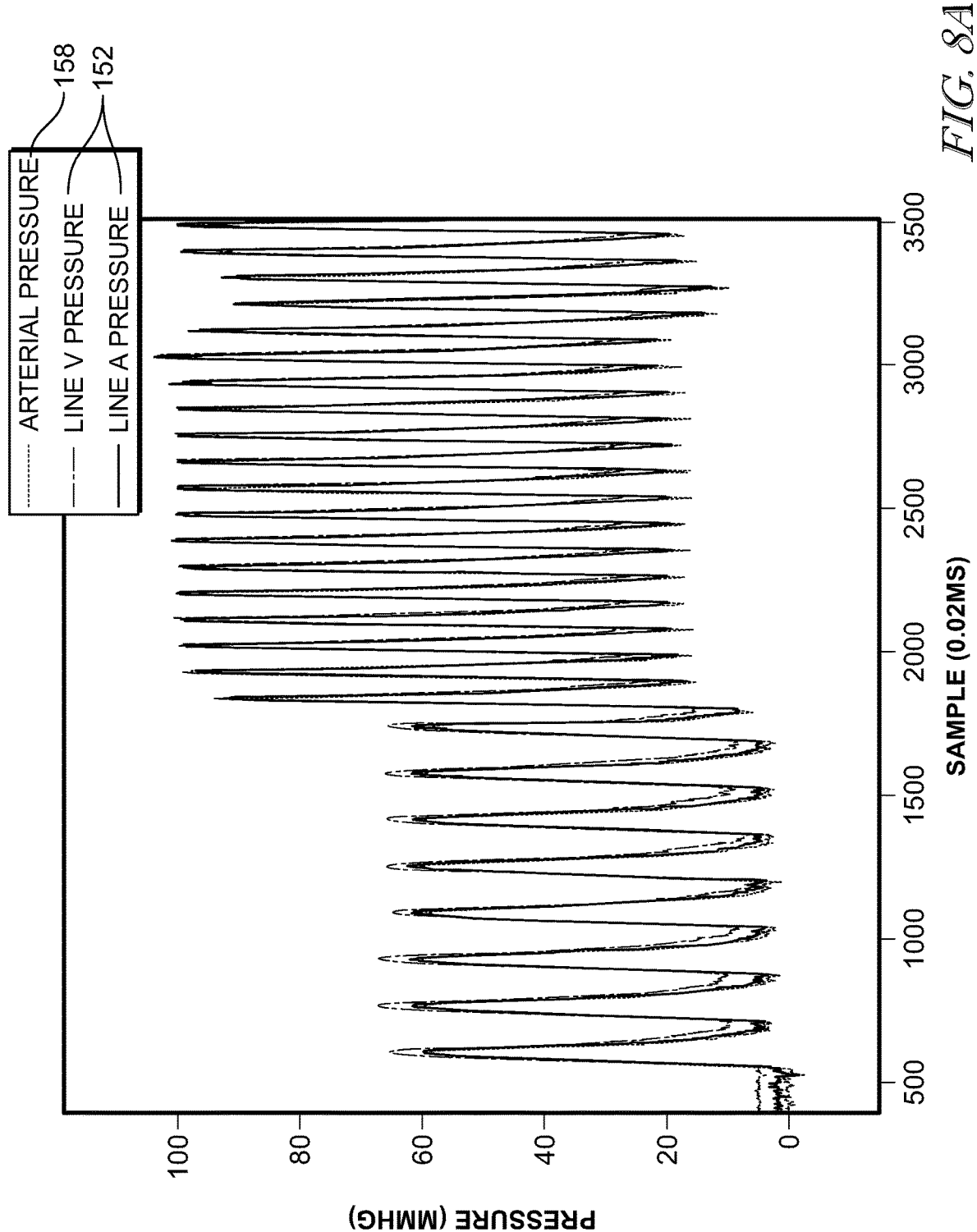
FIG. 8A traces blood pressure observed by the sensors of either system/apparatus of FIG. 1C or 1D.
Figure 8B:
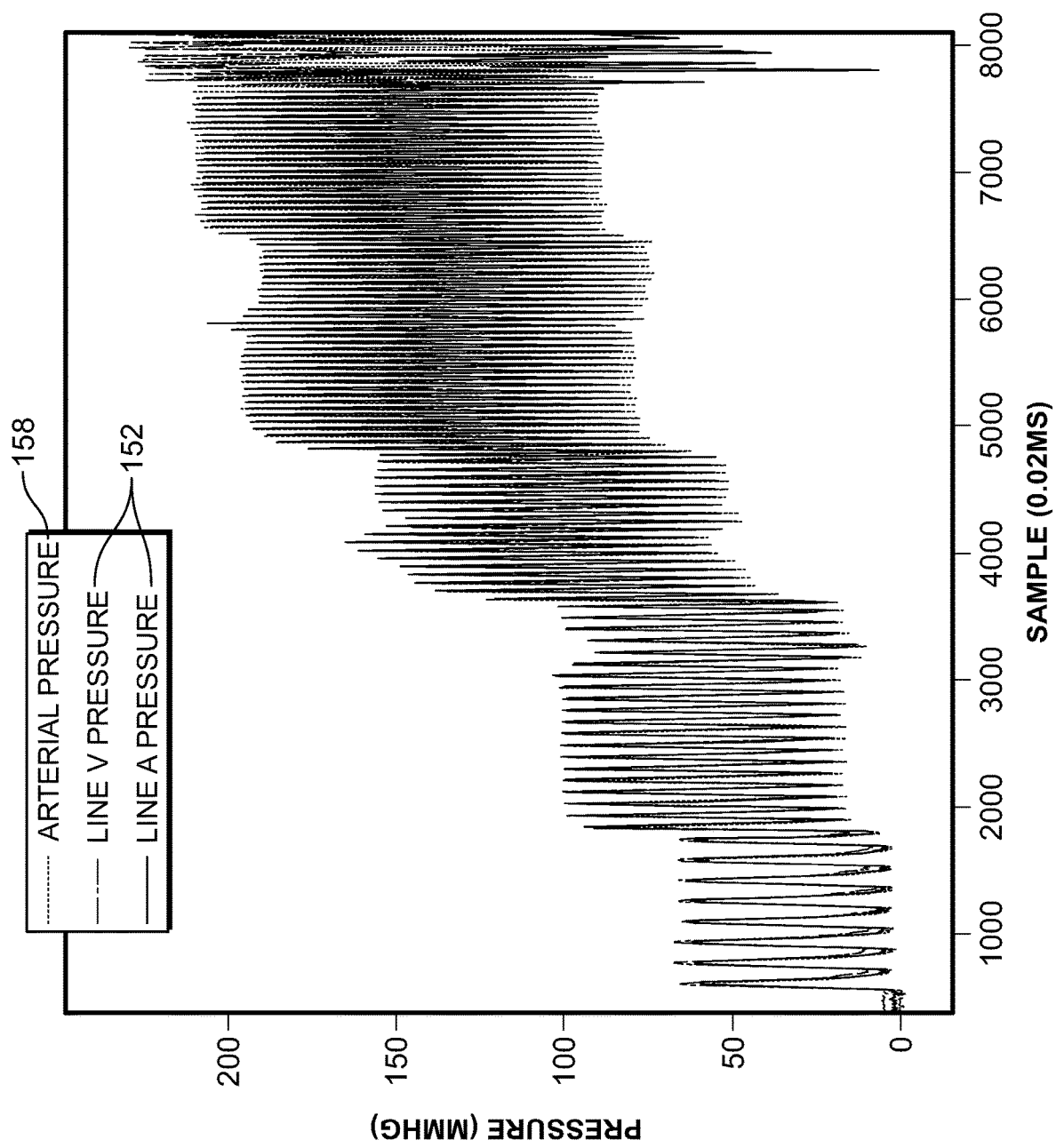
FIG. 8B traces blood pressure changes when a dialyzer switches from an off state to an on state, and step increases in pump speed.
Figure 8C:
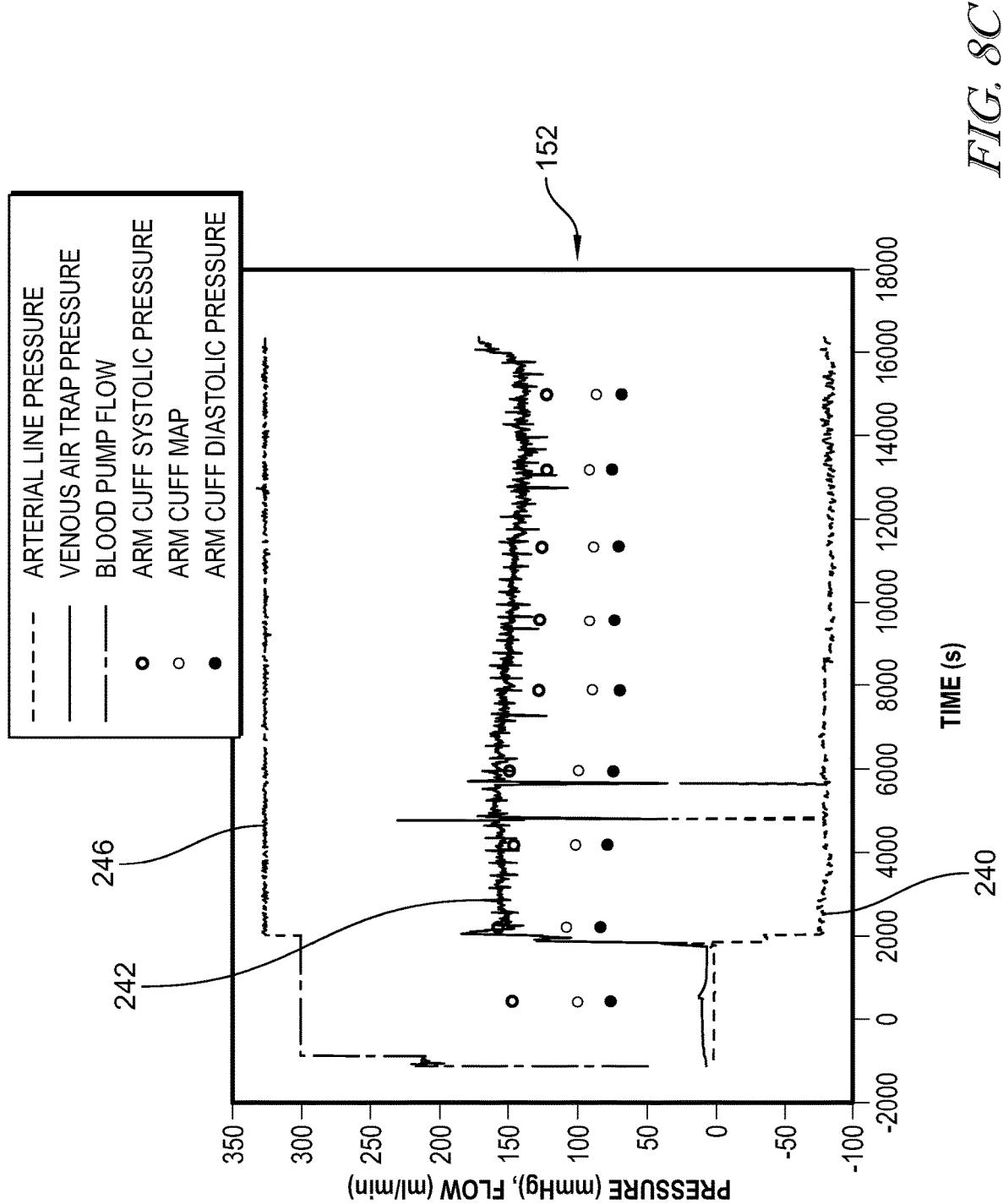
FIG. 8C traces blood pressure changes when a dialyzer switches from an OFF state to an ON state and demonstrate pressure present during operation of a pumping component of the dialyzer.

FIG. 8A illustrates traces of the arriving data 152 from the first and second line sensors 112 and an arterial pressure baseline 158 (as measured by a sensor embedded within the simulator for comparison purposes and algorithm development purposed). The traces of the data 152 graphed here represent pressure over time before the dialysis machine begins operation. During this phase, a Fourier series model of the Fourier series real-time filter 154 is adapted to the waveforms to identify fundamental and harmonic components present in the waveforms as a control analysis, as the waveforms of FIG. 8A represent the undialyzed blood pressure waveforms. Therefore, these waveforms comprise information about the effects of measuring the blood pressure from within the dialysis lines. A comparison of the data 152 provided by the line sensors 112 and the blood pressure baseline 158 reveals measurement and detection effects of the sensor placement within the dialysis lines caused by the structure and configuration of the lines and the selected sensor interface 120, 130, 140. FIG. 8B graphically illustrates the point in time when the dialysis machine begins operation as observed through the measured line pressures. Referring now to FIG. 8C, the data 152 provided by the line sensors 112, including arterial line air trap pressure 240, venous air trap pressure 242, and a pump flow rate 246 associated with the dialyzer 200 during use, is graphically represented. The pump flow rate 246 (i.e., blood flow through the dialysis machine) is calculated via Fourier analysis from the venous air trap pressure data 242.

Figure 9A:
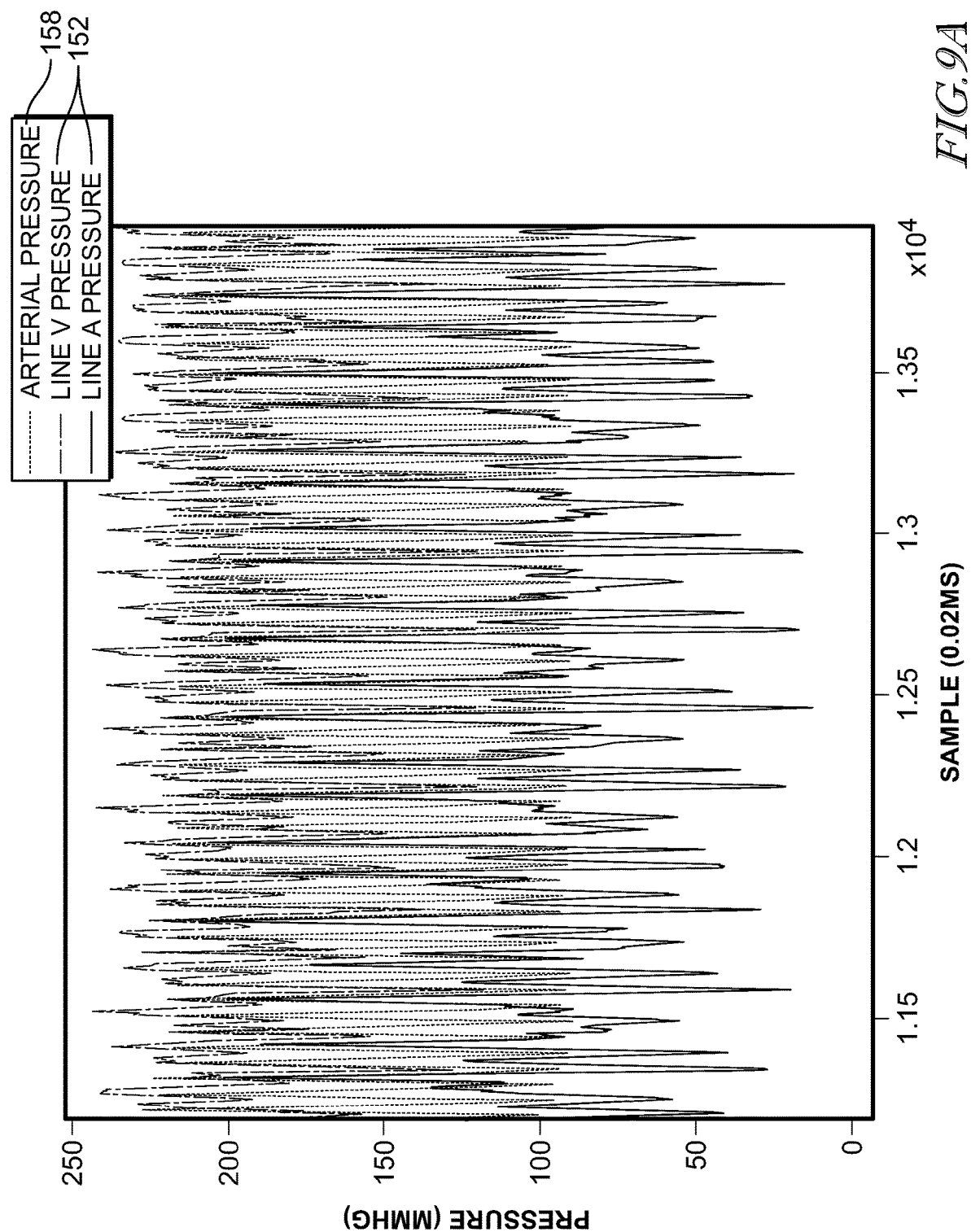
FIG. 9A traces blood pressure observed by the sensors when the dialyzer is operational.
Figure 9B:
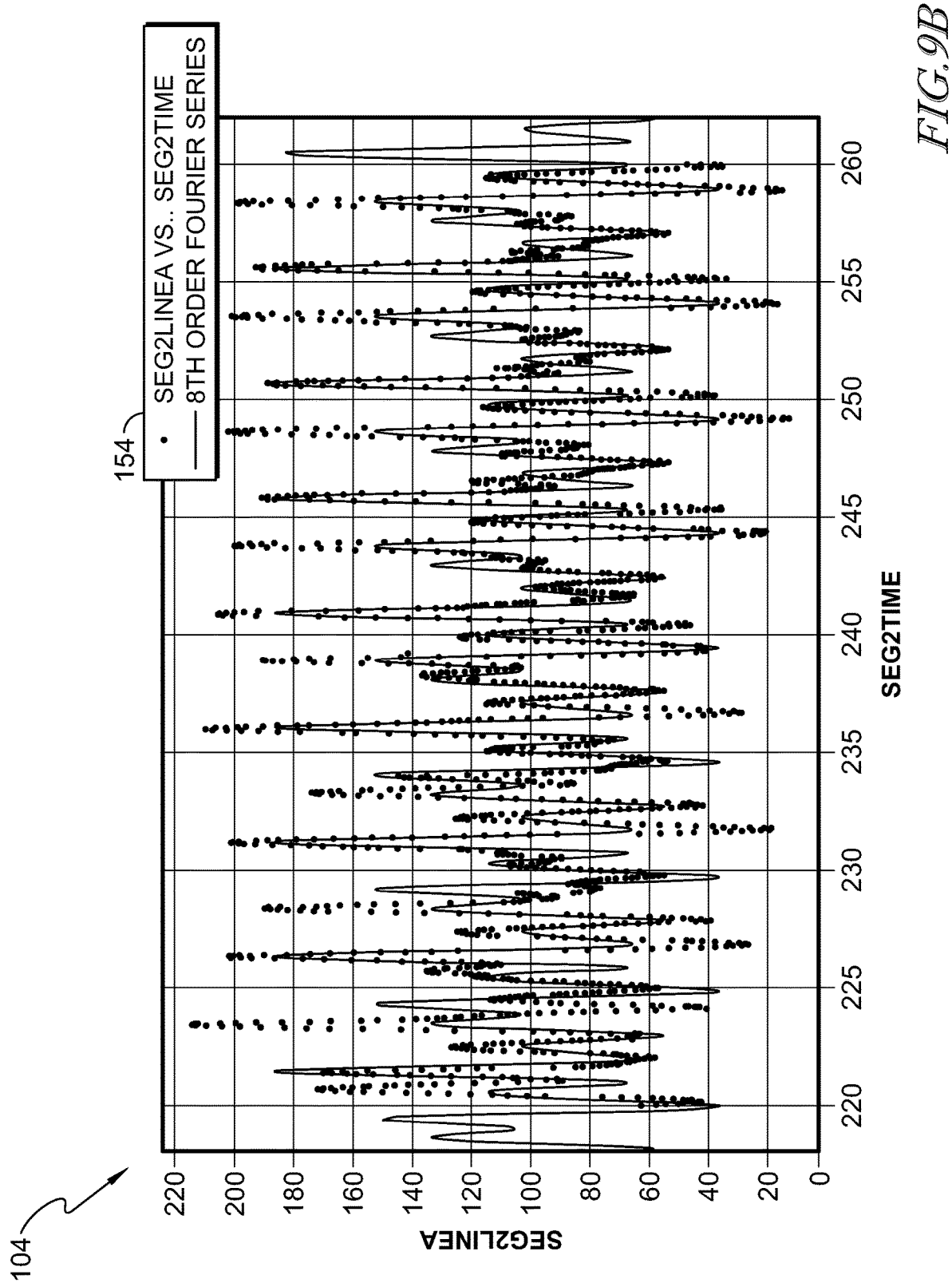
FIG. 9B is the blood pressure information of FIG. 9A transformed into the frequency domain.
Figure 10:
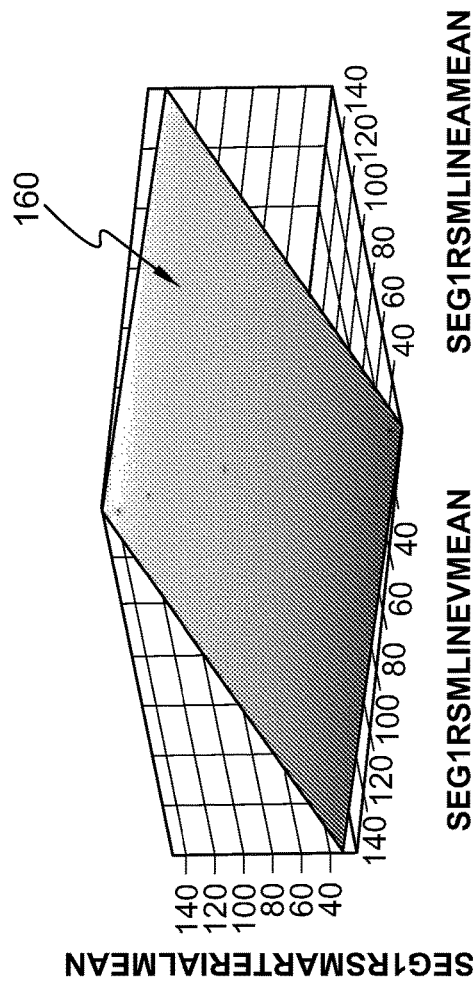
FIG. 10 represents the relationship between dialyzer pump speed and blood pressure data.
Figure 10:
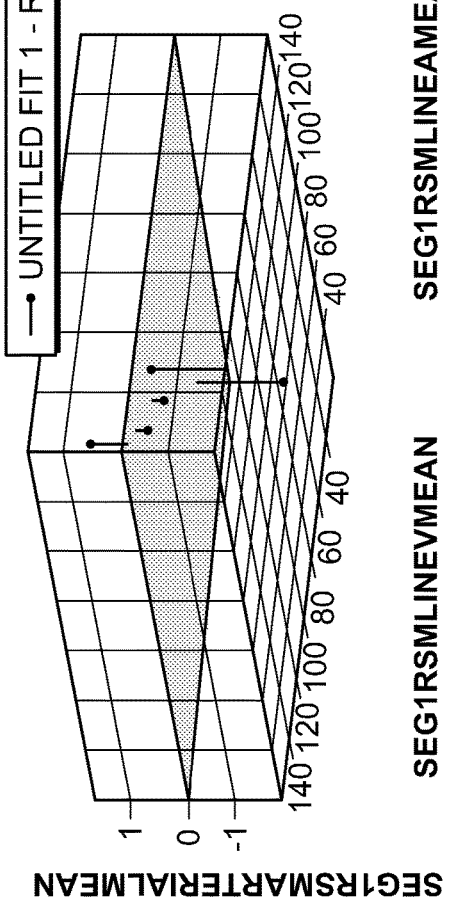
Figure 10:
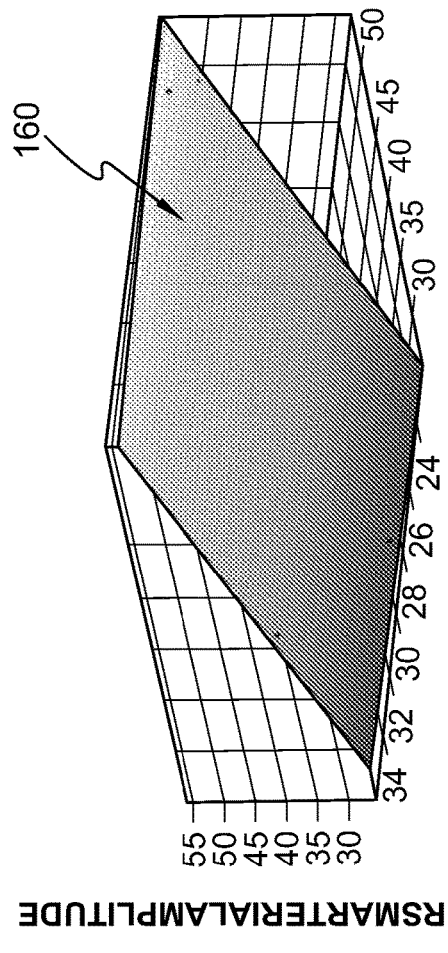
Figure 10:
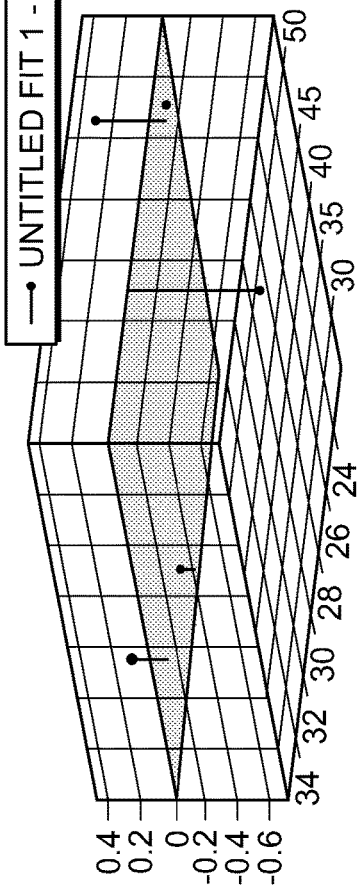

Once the dialysis machine 200 begins operation, the effects thereof on the line pressure are observed in the data 152 acquired by the pressure sensor(s) 112. FIG. 9A illustrates traces of the data 152 acquired by the line sensors 112 and the arterial pressure baseline 158 while the dialysis machine is operational. Notably, the traces again represent pressure over time, but the pressure data from the lines 152 and the baseline arterial pressure 158 both indicate a greater overall pressure and greater peaks in pressure. As with the control analysis, the learning algorithm 104 again adapts a Fourier series model of the Fourier series real-time filter 154 to the waveforms representing the line pressure data 152. This analysis may be performed immediately after startup and/or at any time when the machine is stopped or started to train the adaptive learning algorithm 104 to recognize the effect of the pump on the line pressure waveforms. The learning algorithm 104 may also be augmented by a calibration phase executed during treatment such as for a short period at startup during which the arterial pressure baseline 158 is observed with a finger or arm cuff, for example. Pump speed may be derived through the Fourier analysis performed by the Fourier series real-time filter 154. FIG. 9B graphically represents the Fourier series model (i.e., an $8^{th}$ order Fourier series model) of the line pressure data 152 shown in FIG. 9. Then, the iterative/adaptive learning algorithm 104 builds a model 160 of the relationship between pump speed and the line pressure waveforms in terms of mean and amplitude. The model 160 representing the relationship between pump speed and line pressure data 152 is graphically illustrated in FIG. 10. Adjunct learning allows higher frequency waveform components in the line pressure data 152 to be considered as inputs for reconstructing the higher frequency components in derived line pressure waveforms illustrated in FIG. 9A. The learning algorithm 104 learns the 'shape' of disturbances generated by the dialysis pump and transferred to the dialysis lines across an operating envelope of the system/apparatus 102. The operating envelope comprises pump speed, mean arterial blood pressure, and heart rate. The learning algorithm 104 then subtracts the dialysis pump effects from the line pressures 152 thereby producing line traces representing the derived line pressure waveforms. The derived line pressure waveforms, may, in turn, be reconstructed into the derived arterial blood pressure waveform/trace 150 by a learned model that updates whenever the pump is not running.

Figure 11:
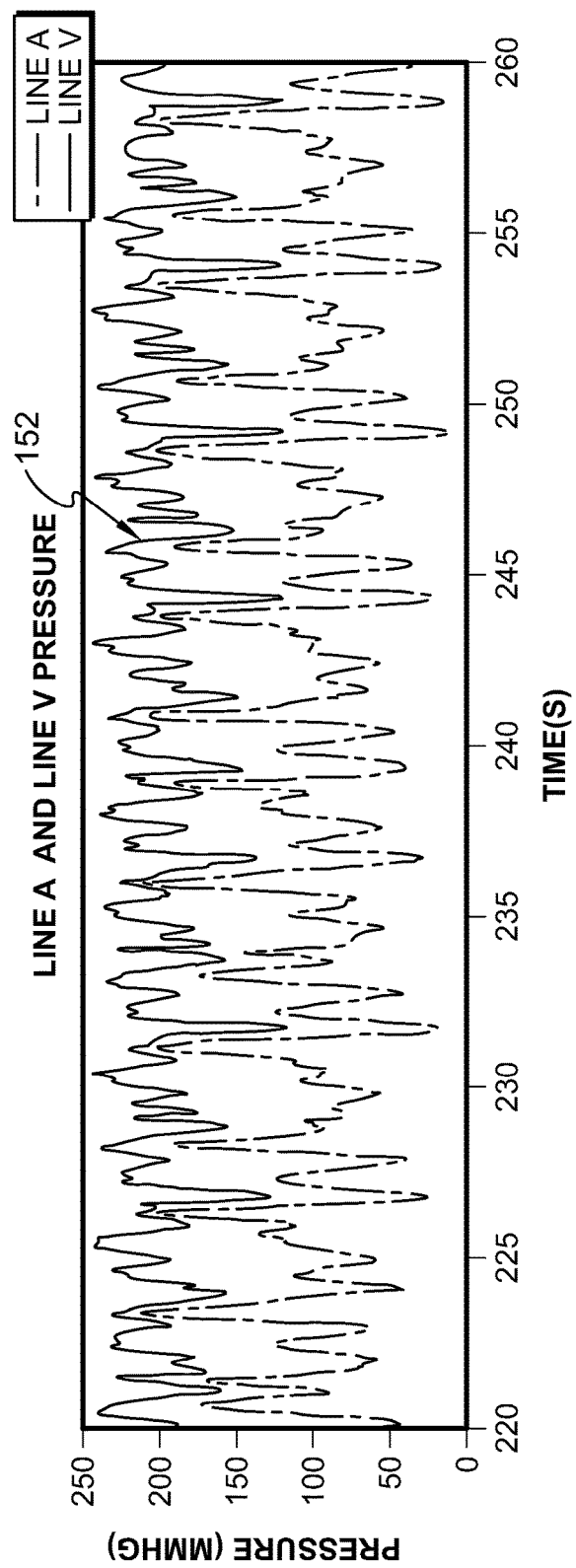
FIG. 11 compares an actual, baseline arterial mean blood pressure to a reconstructed arterial mean blood pressure derived by a learning algorithm.
Figure 11:
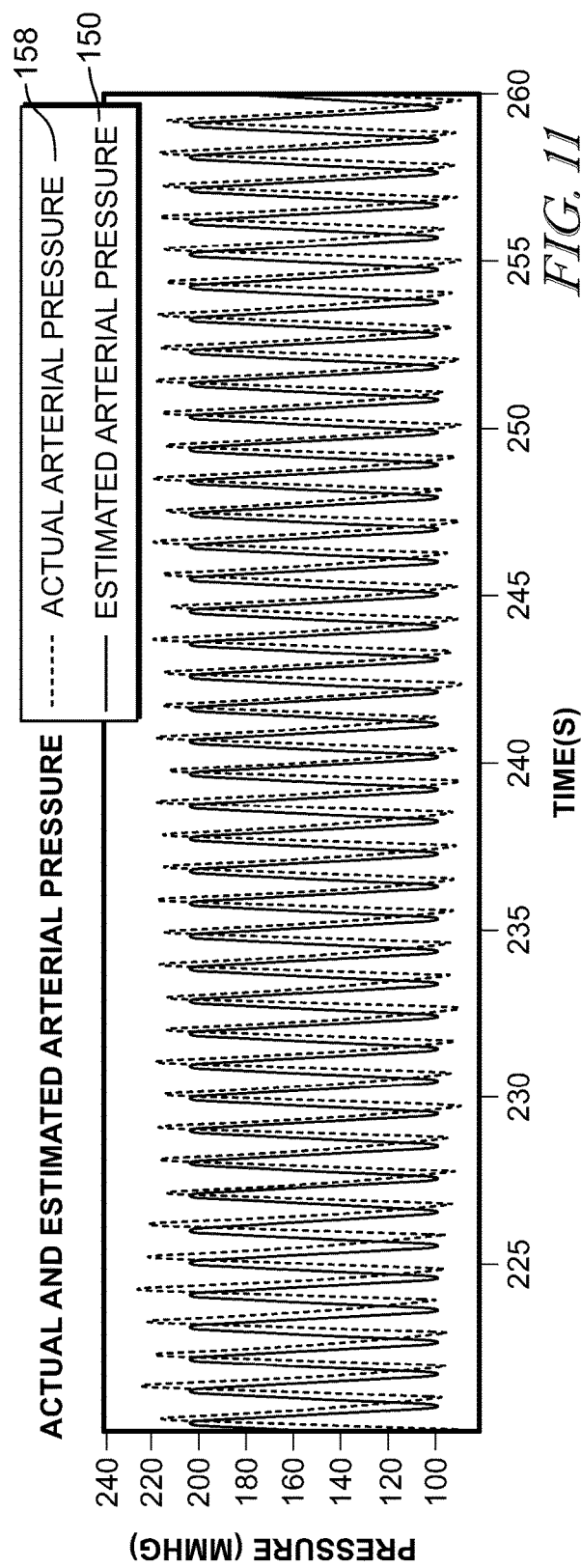

Referring still to FIG. 11, the line pressure waveforms 152 during pump operation in the upper trace are compared with the reconstructed arterial pressure waveform/trace 150 in the lower trace. The lower trace also includes the baseline arterial pressure waveform 158 for direct comparison to the reconstructed arterial pressure waveform 150. In FIG. 11, a slight difference in amplitude between the baseline waveform 158 and the reconstructed waveform 150 may be observed due to the learning algorithm 104 utilizing a lower order model to increase computational efficiency. Diagnostic applications of the learning algorithm 104 may utilize high order models to increase accuracy. The higher order series may capture more complex waveform shapes; in particular, the interaction of the dialysis pump pressure pulsations with the blood pressure pulsations of the patient's heart as observed in the dialysis lines. The order of the model leveraged by the learning algorithm 104 may be adjusted according to availability of computing resources, accuracy considerations, and/or data transfer parameters.

Calculations to derive arterial blood pressure 150 from the dialysis lines pressure data 152, as further discussed with reference to are complex and resource intensive. The calculation is nonlinear, and the calculation varies between patients and between dialysis machines. Still further, the derivation also varies as patient blood pressure and dialysis pump speed change during treatment. The learning algorithm/process 104 described herein throughout applies a signal processing method augmented with an artificial intelligence iterative learning algorithm to develop a model, which allows an estimated arterial blood pressure waveform to be accurately derived from line pressure measurements. The algorithm/method 104 may be applied to real-time data taken from the measurement apparatus 102 or the simulated cardiovascular system 106. The simulated system 106 may be attached to the dialysis machine via standard dialysis lines with sensor access via injection ports, as described hereinabove. The algorithm/method 104 may account for parameters unique to the particular hardware implementing the measurement apparatus 102 or the simulated cardiovascular system 106 including sensor configurations, sensor calibration, sensor settings, pump size, pump speed, and needle size.

Intradialytic hemodynamic instability (i.e., critically high or low blood pressure during a dialysis treatment) is a negative health outcome potentially resulting in long-term consequences including ischemic end-organ damage. Continuous intra-dialytic hemodynamic monitoring (i.e., blood pressure waveform measurement) over sequential dialysis sessions may be analyzed to improve the characterization and prediction of individual responses to dialysis. Data 170 collected by the apparatus 102 and processed by the learning algorithm 104 is then further processed by the predictive algorithm and processing method 108 to develop a patient fingerprint 150 and/or other desirable patient metrics. Particularly, patient metrics and predictions may include correlations between blood pressure trace analysis, physiological health, and disease, and the potential disease identifiers found amongst the data 170.

Analysis of the raw data yields little correlation between the shape of the blood pressure traces and patient physiological and illness history. Further, the 'shape' of the blood pressure waveforms for each patient between treatments is subject to significant variability creating additional obstacles to drawing conclusions or tailoring treatments based upon the raw blood pressure data in the time domain. However, application of the Fourier series real-time filter 154 transforms the raw pressure data from the time domain into the frequency domain. After processing, a shape of the estimated arterial blood pressure responses 150 derived are unique to each patient and are also consistent from treatment to treatment. Therefore, the uniquely shaped response for each patient establishes an individual and identifiable biological fingerprint 172.

The predictive algorithm and processing method 108 may operate on the data 170 and/or the fingerprint 172 to identify biomarkers that function as indicators for designing personalized treatments. Adequate variation exists between the fingerprints 172 of different patients that each fingerprint is indicative of a current and historical state of health and may further provide markers for prediction of future health outcomes. While the fingerprints 172 may be derived from patients undergoing dialysis, fingerprints may instead be derived from data of otherwise healthy patients not in need of dialysis. Still further, when applied to a broader population, the fingerprints 172 may be used as biometric identifiers.

Figure 12A:
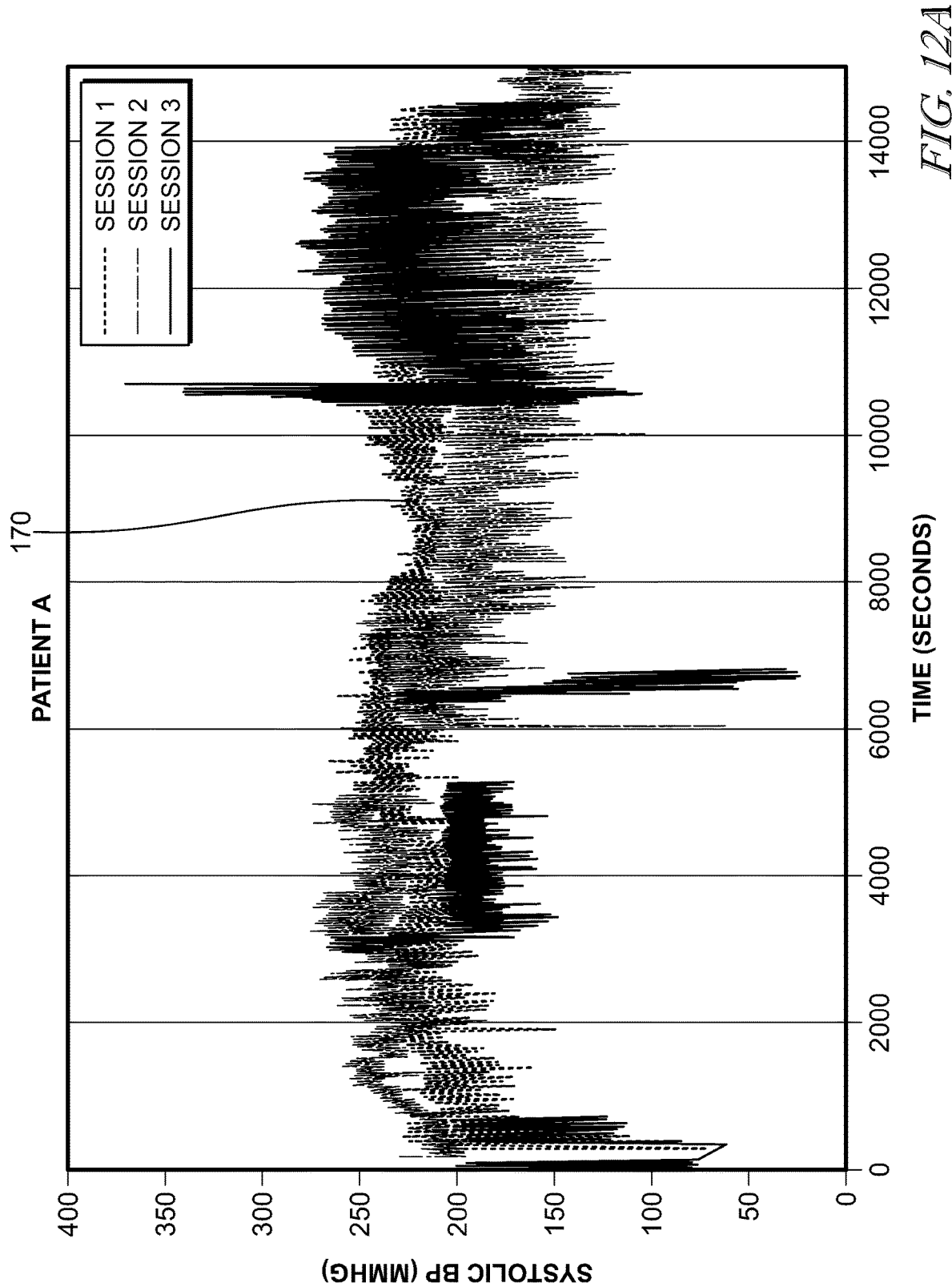
Figure 13:
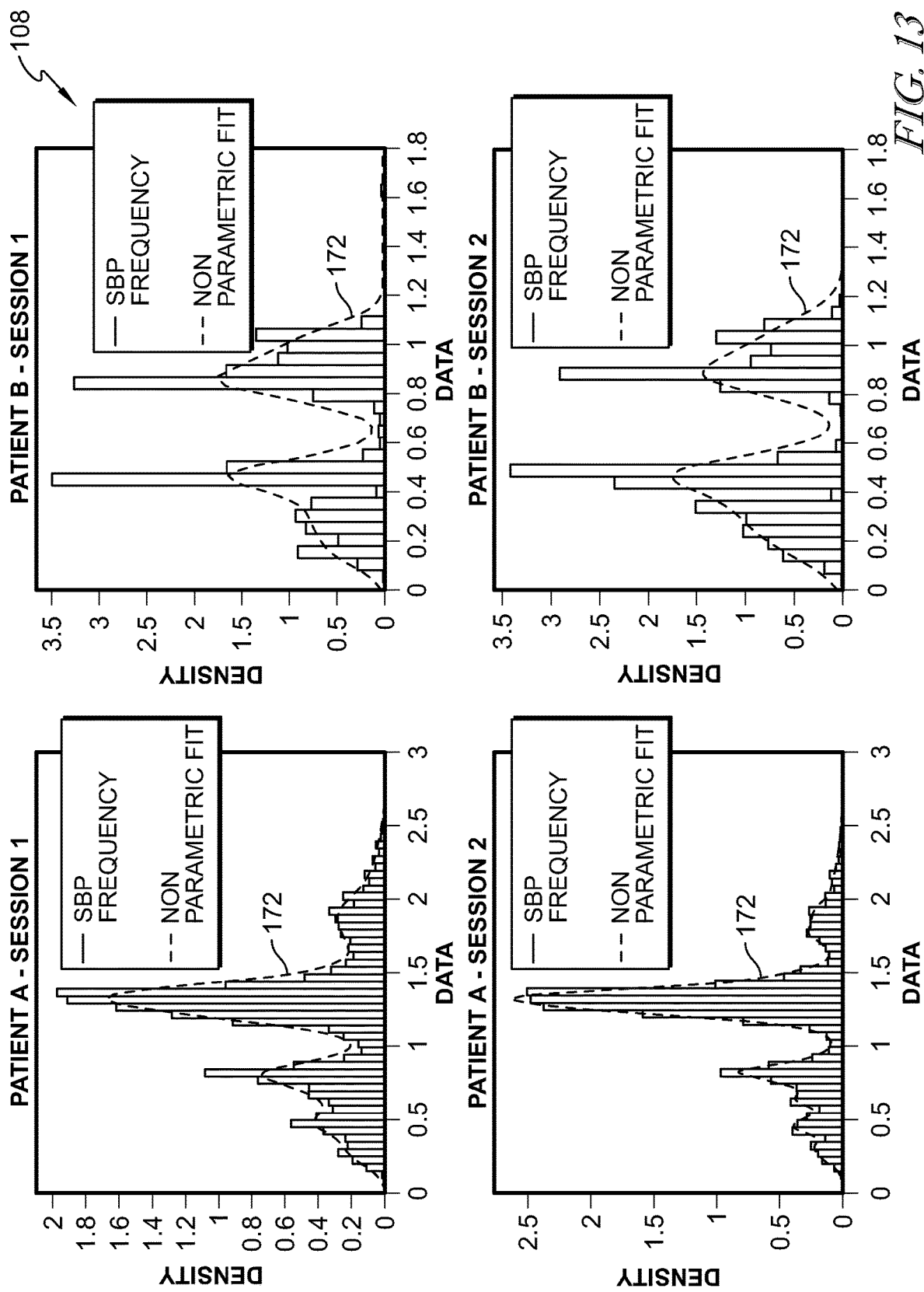
FIG. 13 illustrates histogram plots for a frequency response of systolic blood pressure.
Figure 13:
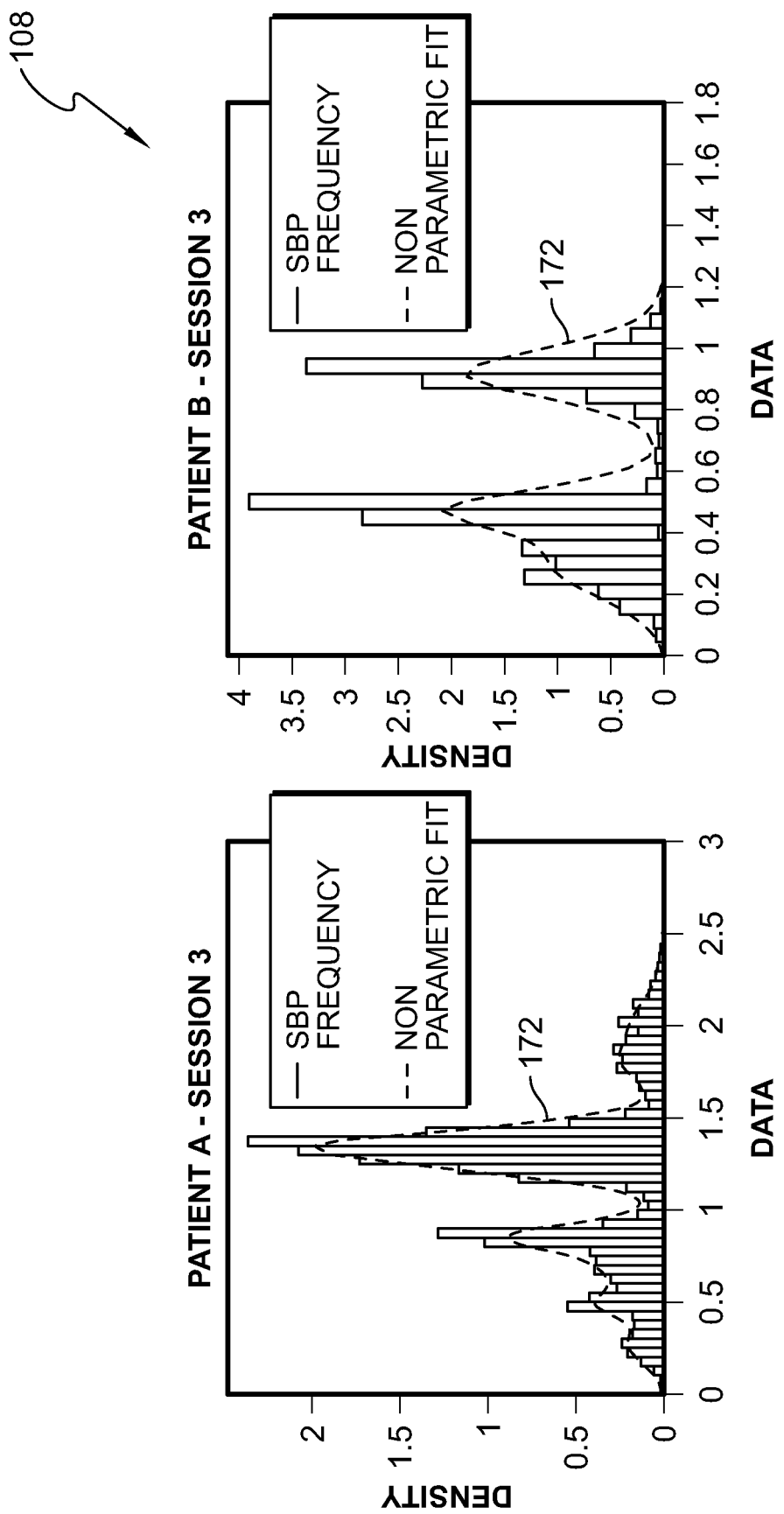

Real-time line blood pressure waveforms 152 are collected continuously throughout dialysis treatment sessions typically lasting three to four hours. Each four-hour data set comprises a continuous oscillating blood pressure trace. The trace can be characterized by the peaks (i.e., systolic pressure) and troughs (i.e., diastolic pressure) of each heartbeat, as noted hereinabove. By joining the peaks, the Systolic waveform is obtained; and by joining the troughs, the Diastolic waveform is obtained. FIGS. 12A and 12B are representative of the systolic data 152 acquired by the measurement apparatus 102 over a typical four-hour dialysis treatment.

FIG. 12A is a typical set of systolic blood pressure traces taken for three consecutive hemodialysis treatments for one patient (Patient A). They show no discernable consistency and vary considerably, not only between sessions, but also during sessions. Analysis of the data shows no identifiable individual consistent characteristics in the time domain (i.e. waveforms of blood pressure over time).

FIG. 12B is a typical set of systolic blood pressure traces taken for three consecutive hemodialysis treatments for another patient (Patient B). Again, there is no consistency either during or between sessions. Still further, when comparing Patient A and Patient B, a marked difference is present between patients.

FIGS. 12A and 12B illustrate a comparison of continuous systolic blood pressure in the time domain as measured across three consecutive hemodialysis treatments, for first and second patients (i.e., Patient A in FIG. 12A; Patient B in FIG. 12B). These charts represent the significant variability between detected systolic blood measure during dialysis treatments. Further, different trends emerge in subsequent treatment sessions for the same patient.

The reconstructed central aortic waveform 150 facilitates calculation of numerous continuous hemodynamic variables/data 164 including pulse rate and systolic blood pressure (SBP in the FIGS.). The hemodynamic data 164 generated by the iterative learning algorithm/processing method 104 may then be analyzed further by identifying frequency and amplitude for local extrema points (i.e., maxima and minima) of systolic blood pressure data. The systolic blood pressure trace data 170 is run through a digital filter, which identifies the points where the trace reaches a maximum (or minimum) point and reverses direction. To better remove noise and smooth the data, extrema below a certain width are disregarded in example embodiments. Useful data points observed include the blood pressure value and time value recorded for each instance of an extrema. The time and amplitude differences between each successive extrema event may also be recorded.

The modified short-time Fourier transform filter 154 is then applied to the smoothed data as a moving asynchronous filter to extract the sinusoidal frequency and phase content of the time-varying filtered systolic blood pressure signals/waveforms 152. A conventional Fourier transform performs calculations on sections of data of equal duration, but here the filter 154 is adaptive in order to process a time varying system. This results in transformation of the systolic blood pressure data 152 into the frequency domain, which, in turn, is a representation that is one level of abstraction away from the time domain. Further, differences in time and blood pressure between each current extrema point and the next extrema point instance provide additional information for development of the patient fingerprint(s) 172. The extrema point blood pressure difference (amplitude) and time difference (frequency) data may then be plotted as histograms that represent all the extrema point data by the numbers of instances in the data for each level of quantization. These spectra are then decomposed into constituent frequency events (i.e., bins of a particular width) using the Freedman-Diaconis rule, and plotted as histograms (see FIGS. 13, 14A, and 14B) for each individual patient. Further, sum of squares estimation may be used to quantify the variability during and between treatments as well as the variability between patients.

The predictive algorithm and processing method 108 analyzes the interactions between the physical parts of the cardiovascular system (e.g., heart rate, stroke volume, blood vessel resistance, blood vessel compliance, etc.) and the control system (nervous system, brain, baroreceptors, baroreflex, etc.). The control system attempts to regulate the blood pressure towards increased stability. The extrema points of the systolic blood pressure data 152 represent interactions between the control system and the physical system (e.g., the extrema indicate successful curtailing of a volatile blood pressure). The control interactions may then be further characterized by approximating a trace passing through the extrema points with a sinusoid having variable amplitude and frequency. Finally, the sinusoid values are collected into a number of bins bounded by one of amplitude and frequency depending on the particular characteristic of interest.

In an experimental example, forty-four participants completed three dialysis sessions with continuous, non-invasive hemodynamic monitoring. Of the participants, 61% were males, mean age was 62.3±16 years, and 43% had diabetes. Analysis of conventional hemodynamic parameters revealed expected intradialytic trends (e.g., a gradual near-linear decline in blood pressure, cardiac output, and stroke volume; and a rise in total peripheral resistance). However, there was significant intra-individual variation in measured systolic blood measure and hemodynamics between dialysis sessions (see FIGS. 12A and 12B). In contrast, frequency analysis of beat-to-beat blood pressure trends indicated a characteristic pattern of results unique to each individual and reproducible for the individual across different dialysis sessions, as shown by the histogram frequency response plots of systolic blood pressure in FIGS. 13, 14A, and 14B.

Figure 14A:
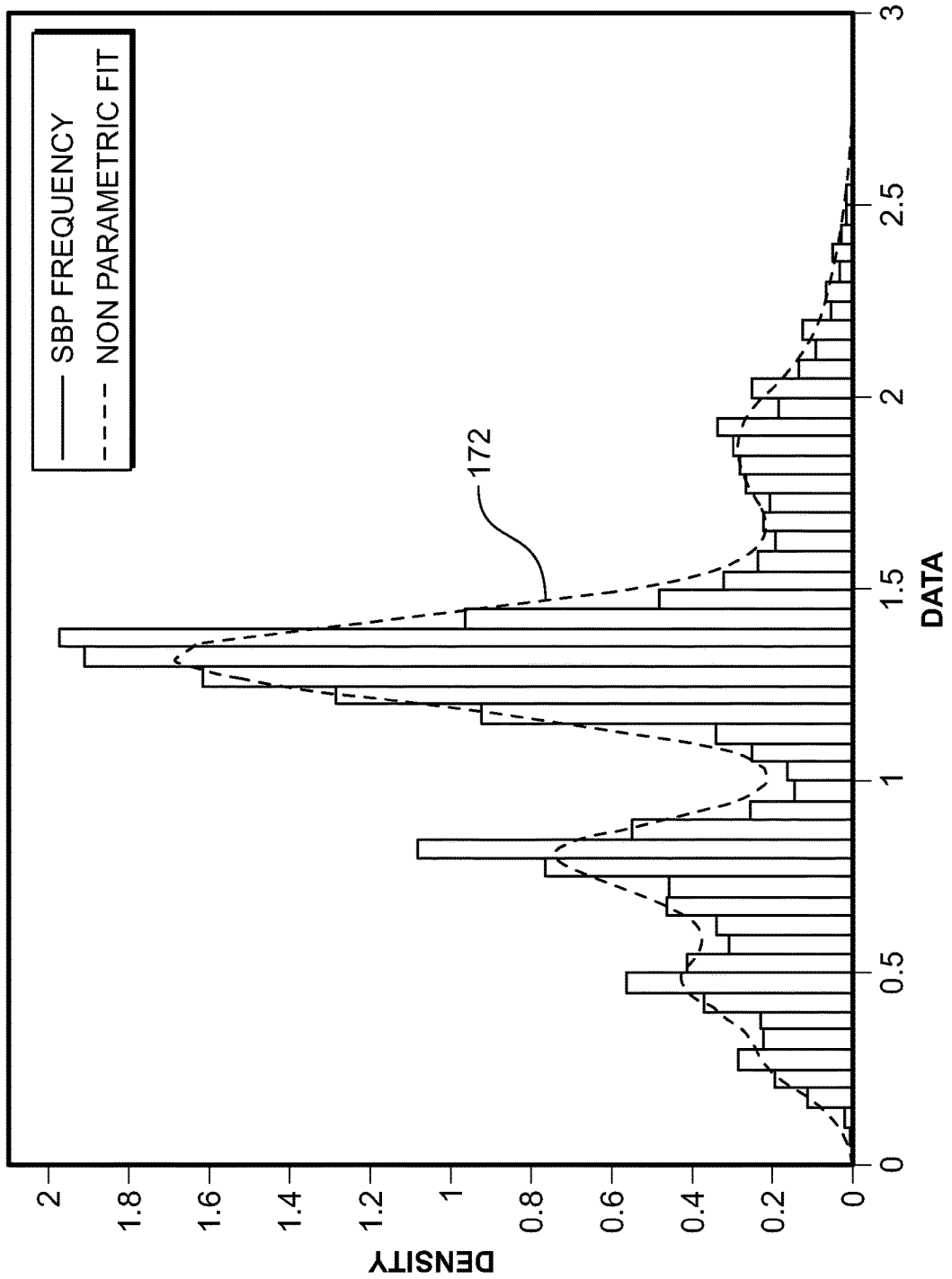
FIG. 14A is a histogram plot for Patient A enlarged from FIG. 13.
Figure 14B:
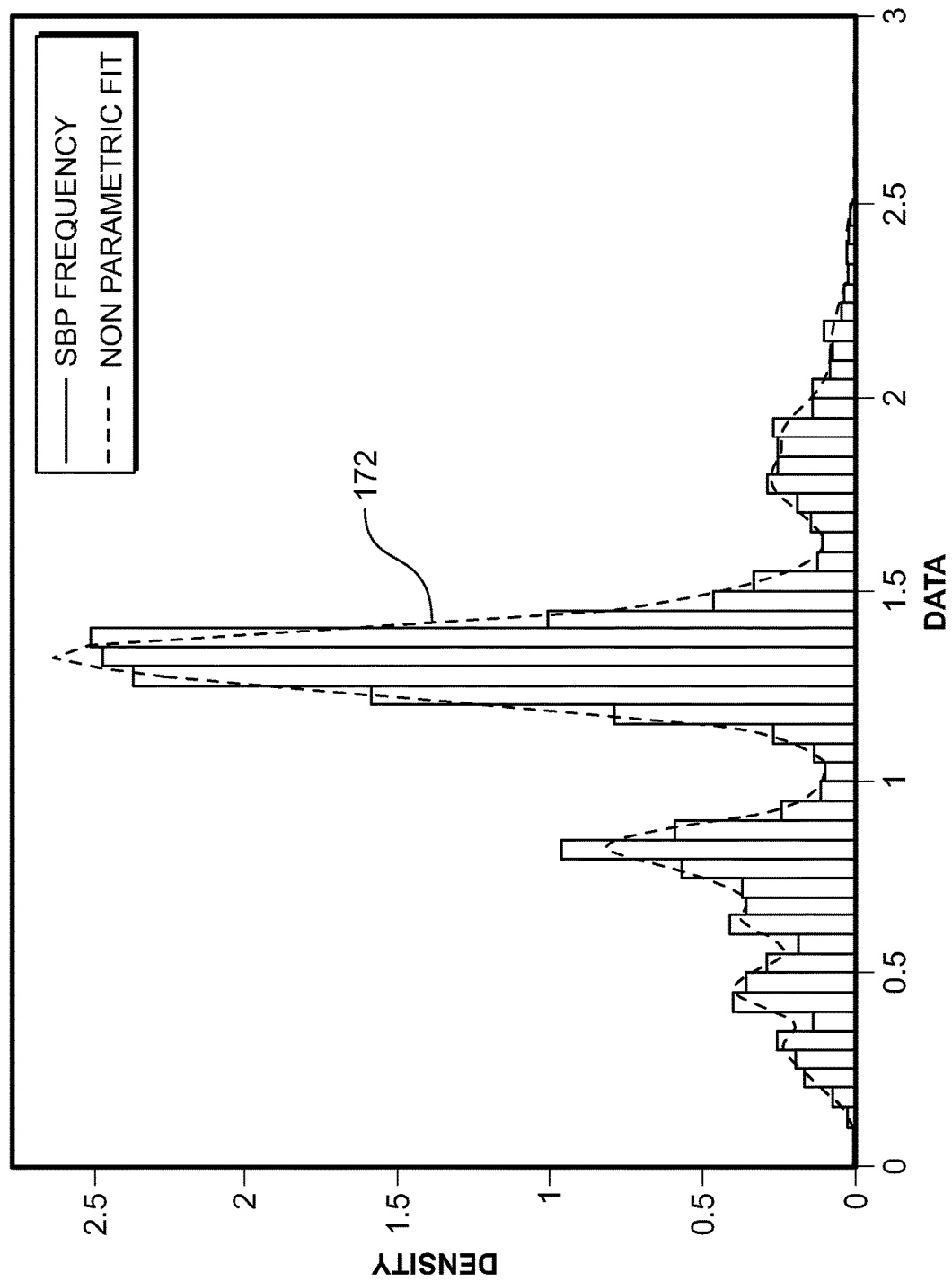
FIG. 14B is a histogram plot for Patient B enlarged from FIG. 13.
Figure 14C:
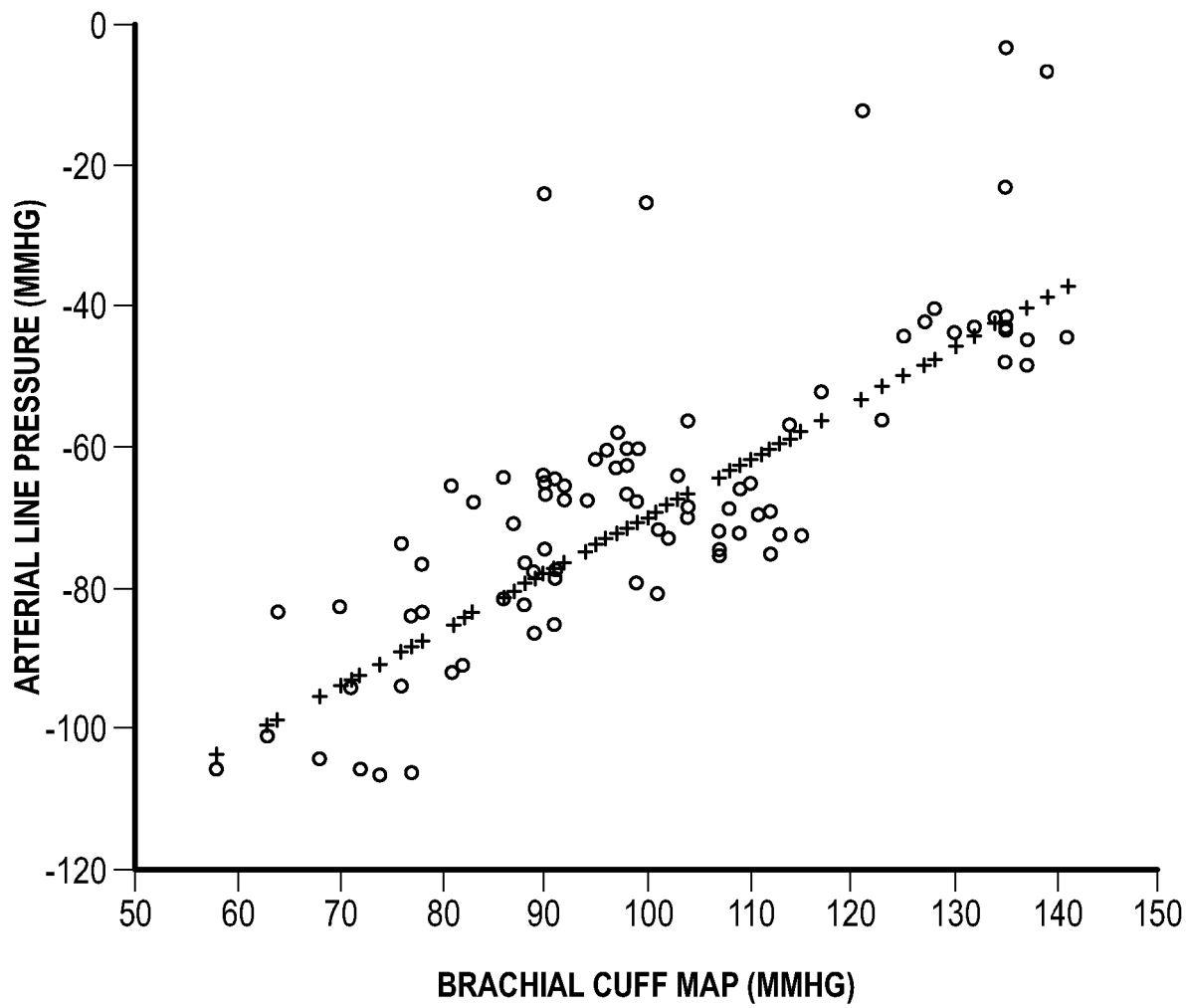
FIG. 14C is a scatter plot displaying raw data from a patient study demonstrating the relationship between brachial artery pressure as measured by an arm-cuff and the corresponding arterial line pressure measured (by a non-invasive blood pressure monitoring system/apparatus of FIG. 1D or 1E) over a number of dialysis sessions (o) with least squares linear fit (+)
Figure 14D:
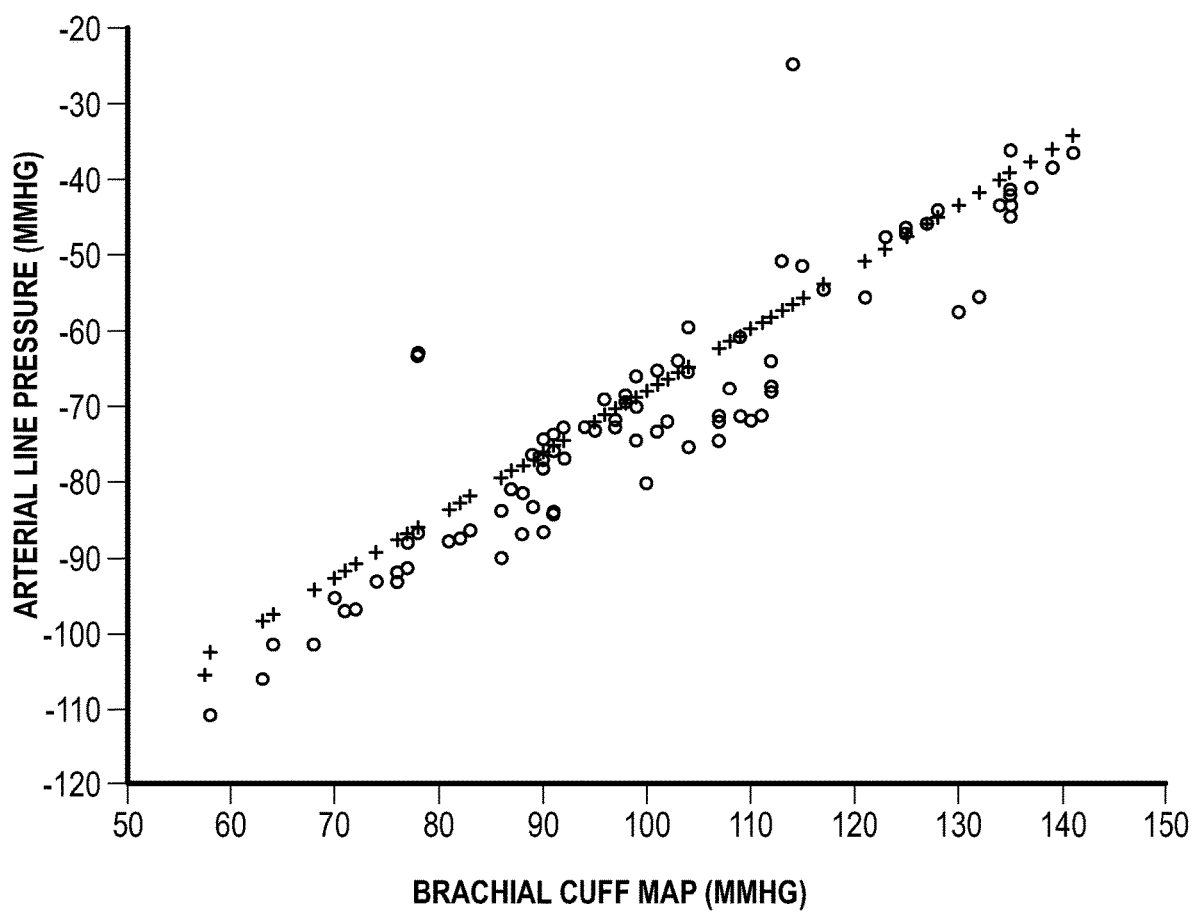
FIG. 14D is a scatter plot displaying raw data from a patient study demonstrating the relationship between brachial artery pressure as measured by an arm-cuff and the corresponding arterial line pressure measured (by a non-invasive blood pressure monitoring system/apparatus of FIG. 1D or 1E) over a number of dialysis sessions (o) with least squares linear fit (+) following compensation for time-varying effects during treatment.

FIG. 14C is a scatter plot displaying raw data from a patient study demonstrating the relationship between brachial artery pressure as measured by an arm-cuff and the corresponding arterial line pressure measured (by a non-invasive blood pressure monitoring system/apparatus of FIG. 1D or 1E) over a number of dialysis sessions (o) with least squares linear fit (+). Referring to FIG. 14D, a scatter plot displays raw data from a patient study demonstrating the relationship between brachial artery pressure as measured by an arm-cuff and the corresponding arterial line pressure measured (by a non-invasive blood pressure monitoring system/apparatus of FIG. 1D or 1E) over a number of dialysis sessions (o) with least squares linear fit (+) following compensation for time-varying effects during treatment. The linear relationship revealed by FIG. 14D confirms that the non-invasive blood pressure monitoring apparatus 102 accurately estimates blood pressure continuously and non-invasively. This linear relationship is derived after adjusting the data for time varying effects over the 4-hour long treatments and correcting for differences in blood pump flow between individual patients.

Variability in time-domain hemodynamic measures between dialysis treatments is an obstacle to characterization of individual patient responses. In contrast, frequency analysis of systolic blood pressure changes during dialysis remains consistent for individuals and may further provide a descriptor of cardiovascular response to hemodialysis that is unique to each individual patient and may be informative for predicting patient outcomes.

The learning algorithm 104 and the predictive algorithm 108 may together operate as a compound algorithm that takes difficult to interpret time-varying data and translates it into the frequency domain to generate the stable, unique patient fingerprint 172. The patient fingerprint(s) 172 may be correlated with aspects of physiological well-being and/or disease. The compound algorithm and the patient fingerprint (s) 172 may track and/or predict physiological degradation, identify physiological metrics for personalized treatments, facilitate generation of biometrics, and identify treatments based on patient groupings, particularly patient groupings in connection with contraindications. For example, the predictive algorithm 108 of the compound algorithm may predict instances of hypotension during dialysis and/or the likelihood thereof.

Figure 15:
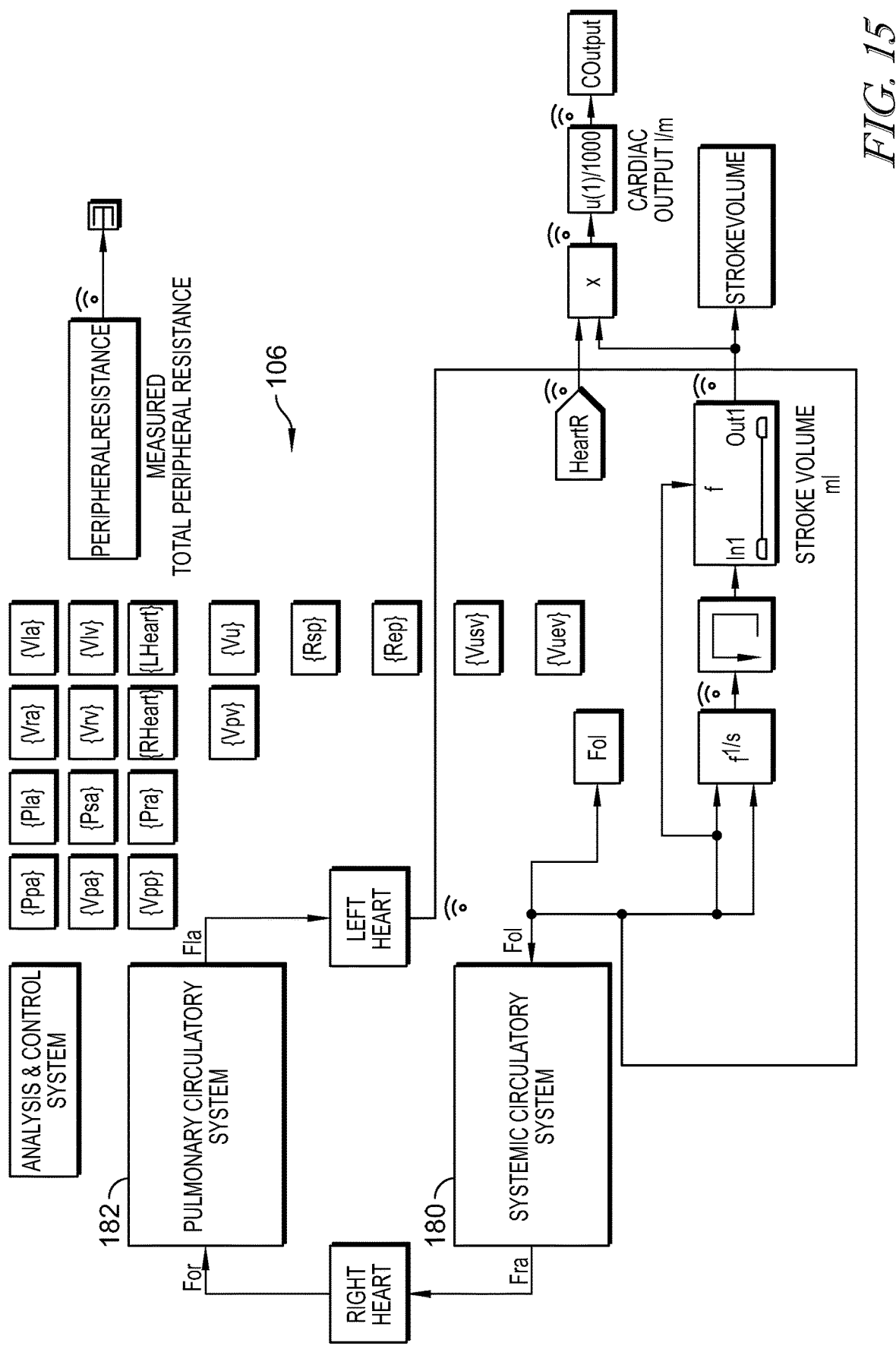
FIG. 15 illustrates a software example of the simulated cardiovascular system of FIG. 1C.
Figure 15:
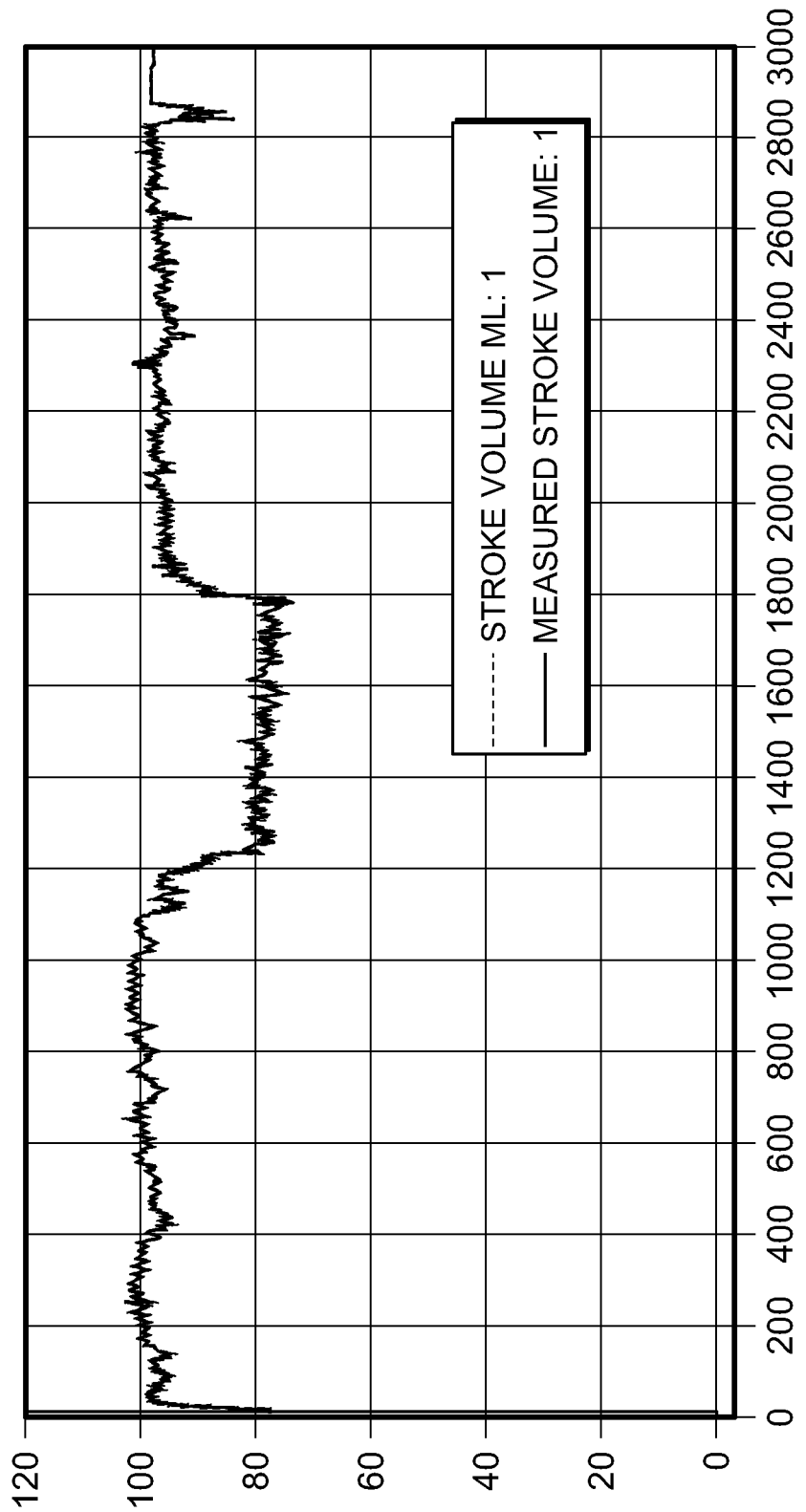
Figure 15:
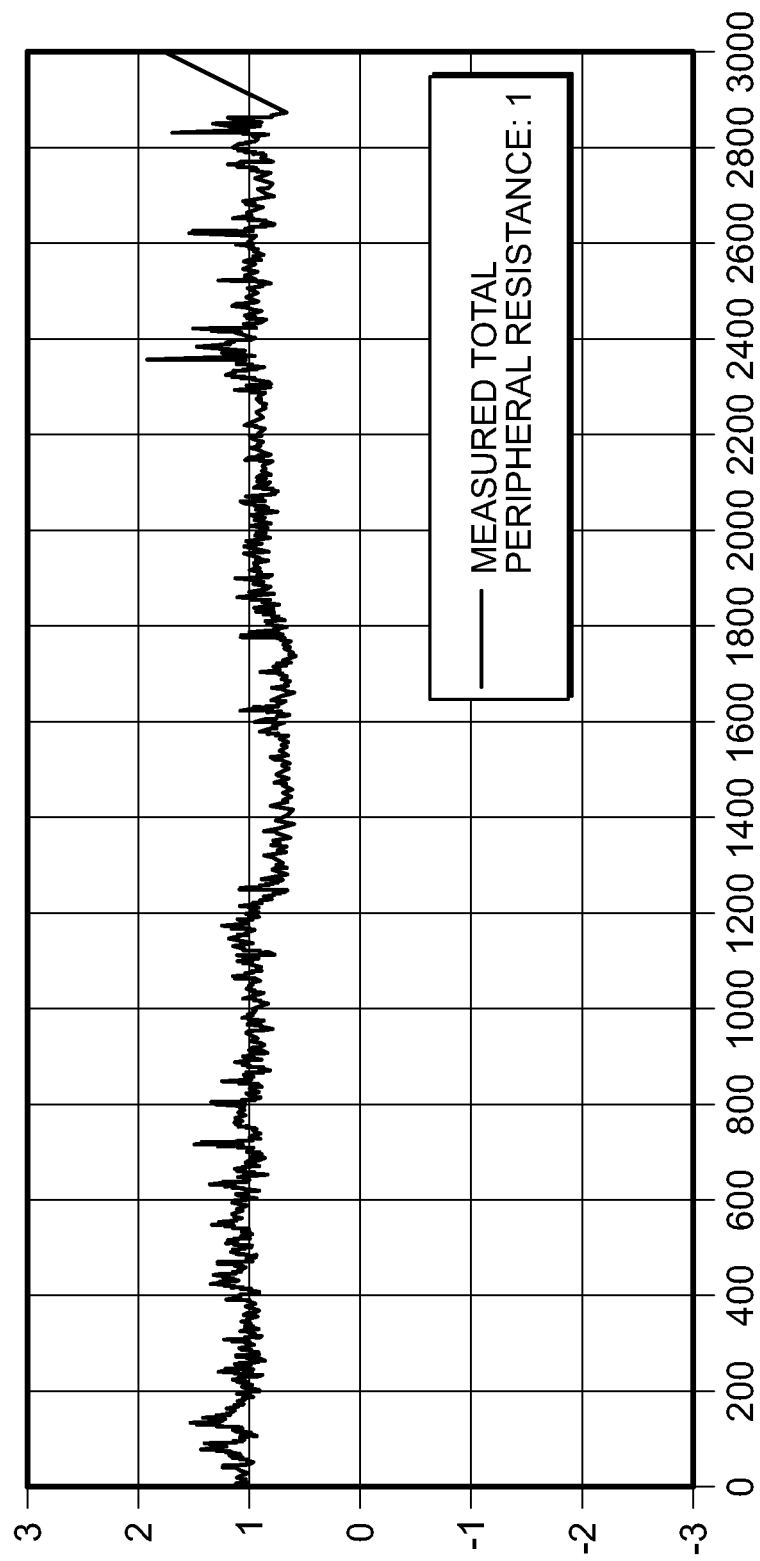

FIG. 15 illustrates a software embodiment of the simulated cardiovascular system 106. The simulated cardiovascular system as diagrammed in FIG. 15 models one or more blood pressure receptors, models a patient nervous system/systemic circulatory 180, and a patient pulmonary system 182. The simulated cardiovascular system 106 facilitates investigation of individual patient control systems. The simulated cardiovascular system 106 may account for a plurality of physical parameters and such parameters may be adjusted by artificial intelligence according to observed patient data acquired during laboratory experimentation or other implementations of the measurement apparatus 102. The predictive algorithm 108 discussed herein throughout may be similarly applied to the simulated cardiovascular system 106.

A number of components algorithms and processes together comprise the learning algorithm and method of process 104. First, a calibration algorithm calibration algorithm calibrates the measurement apparatus 102, including the sensors 112 thereof. During an example calibration, the incoming Line V and Line A pressure waveform data 152 may be fitted to a first order Fourier model via recursive least squares calculations in moving windows wherein the moving windows are selected as twice the period of the heartbeat. This example moving window selection ensures adequate data points and may reduce instances of overfitting. The calibration algorithm outputs four parameters for each of Line A and Line V including: $a_0$ mean value of the line, $a_1$ Sine parameter, $b_1$ Cosine parameter, and/or w fundamental frequency. The fundamental frequency corresponds to the patient heart rate. Referring back to FIG. 7A, mean line values are shown for Line A and Line V.

The learning algorithm 104 is a multi-dimensional surface which links inputs (e.g., estimated heart rate (w), mean Line A pressure, mean Line V pressure, etc.) and outputs the estimated/reconstructed mean arterial pressure 150. In an example embodiment, this relationship is expressed as a polynomial of the variables, which is fitted to the data via a standard least squares estimator for the polynomial coefficients. This calculation is known as the response surface methodology. Again, to decrease the likelihood of overfitting, the line pressure data 152 from which the polynomial is updated is sampled at a relatively low rate and is triggered by one of a notification of a calibration phase and triggering from an expert system.

The expert system may be pre-programmed, based on observations made during experimental operation of the measurement apparatus 102 or data collected from patients. Further, the multi-dimensional surface of the learning algorithm 104 may be updated every time the patient wears a finger or arm blood pressure cuff. Segments of FIG. 7A illustrate phases of the data processing as follows:

a: During a calibration phase Line A and Line V values are within a pre-determined distance from a cuff-measured mean arterial pressure. This indicates that the dialysis pump is off. The multi-dimensional learning surface may be updated from Line A and Line V pressure data 152 fitted to cuff-supplied blood pressure data.

b: Next, a dialysis pump is switched on causing Line A and Line V pressures to diverge significantly indicating to the expert system that the pump is on. Further, the cuff blood pressure data may still be available. The multi-dimensional learning surface is updated from the Line A and Line V pressure data 152 being fitted to the cuff-supplied blood pressure data.

c: during an operational phase, the blood pressure cuff may be removed (perhaps for patient comfort). During and after this stage the green trace of FIG. 7A represents the estimated mean arterial blood pressure 150 from the learning algorithm 104. The Line A and Line V pressures 152 both decrease and increase in pressure indicating changes in arterial pressure rather than changes in pump speed.

d: The Line A and Line V traces 152 diverge, but the mean thereof remains constant indicating stable blood pressure and an increase in dialysis pump speed.

e: During this phase, estimated mean arterial pressure 150 drops, and venous pressure remains constant, indicating saturation of the venous sensor. Latching the current predicted value until normal operation resumes may ensure improved performance of the learning algorithm 104.

f: At this stage, normal operation and reconstruction of the arterial blood pressure 150 resumes (i.e., sensor saturation has been remedied).

Figure 16:
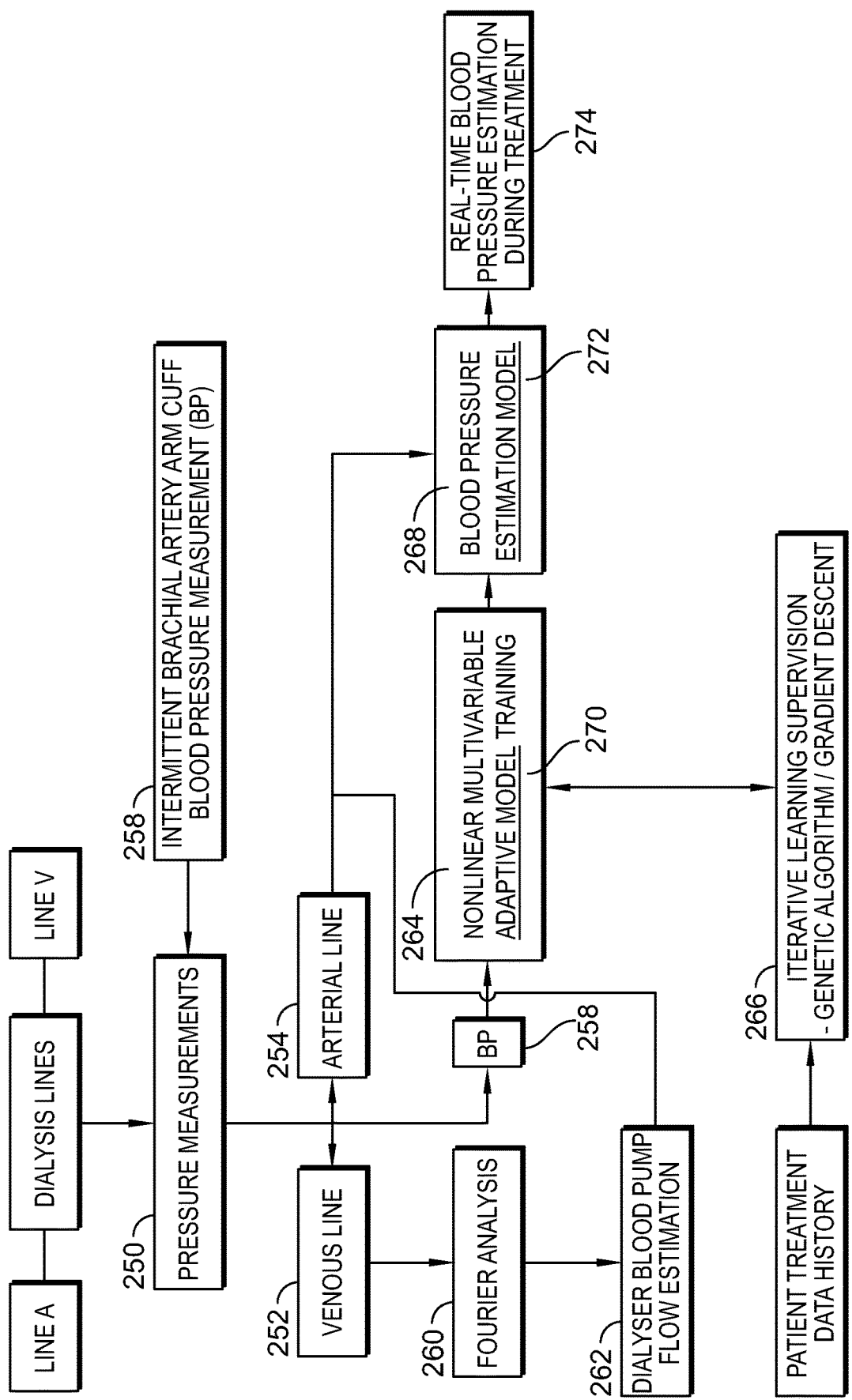
FIG. 16 diagrams operation of the non-invasive blood pressure monitoring system/apparatus of FIGS. 1D and/or 1E.

Referring now to FIG. 16, a flowchart demonstrates the steps/processes for operation of the non-invasive blood pressure monitoring system/apparatus and execution of the learning algorithm 104 stored in the memory 114 and implemented by the processor 110 (see FIGS. 1C and 1E). At step 250, pressure measurements are received by the processor 110. The pressure measurements include venous line pressure measurements 252, arterial line pressure measurements 254, and an intermittent patient blood pressure reading 258 (e.g., a blood pressure cuff measurement)

received from the venous and arterial pressure sensors 112 and patient blood pressure monitor. The venous line pressure measurements 252 undergo Fourier analysis at step 260 and an outcome thereof represents an estimation of blood pump flow rate 262 (i.e., flow rate of blood through the dialyzer). The intermittent patient blood pressure reading 258 is a training input to a nonlinear multivariable adaptive model 270 at step 264. Also at step 264, an iterative learning supervision algorithm 266, which learns from patient treatment histories, data from previous treatment sessions, real-time blood pressure measurements, patient blood pressure history, and algorithmic analysis thereof. In example embodiments, these inputs may be analyzed by a genetic algorithm to optimize, or otherwise improve, the nonlinear multivariable adaptive model 270. Thus, the training and structure of the nonlinear multivariable adaptive model 270 may be supervised by a genetic algorithm (e.g., a meta-heuristic inspired by the process of natural selection and belonging to the larger class of evolutionary algorithms). At a next step 268, the nonlinear multivariable adaptive model and the arterial line pressure measurements 254 are utilized as inputs to generate a blood pressure estimation model 272. After training, the blood pressure estimation model 270, when provided with arterial line pressure measurements 254, in turn generates real-time blood pressure estimation/reconstruction 274 during a treatment session (i.e., hemodialysis). Accordingly, the nonlinear multivariable model 270 is developed by an adaptive algorithm for use by the blood pressure estimation model 272 to reconstruct blood pressure from extra-corporeal blood line pressure sensor observations thereby non-invasively and continuously monitoring blood pressure.

Similar to the learning algorithm 104, the predictive algorithm 108 also comprises a number of underlying algorithms and processes. Considering Patient A shown in FIG. 14A, the x-axis is the extrema point time difference in Hz (i.e., 1/f) and quantized into frequency bins which are 0.05 Hz wide. The y-axis represents the relative numbers of instances in the frequency-domain data for each of the bins. For a given patient, the fingerprint 172 is consistent between treatments and during treatment. Additionally, the patient fingerprint 172 may be derived from only a small segment of the data collected during a typical four-hour dialysis treatment window, without compromising the uniqueness thereof. The patient fingerprint 172 is a natural biomarker and the uniqueness thereof is derived from the individual nature of blood pressure and associated cardiovascular and nervous system physiology.

The body has both short-term and long-term blood pressure regulatory processes. The body attempts to regulate blood pressure to be at a relatively stable and optimal pressure. This is regulation is accomplished via baroreceptors disposed within blood vessels. The baroreceptors sense blood pressure and relay the information to the brain so that a proper blood pressure may be maintained. Information from the baroreceptors triggers autonomic reflexes that control the heart, cardiac output, and vascular system to influence total peripheral resistance. This system-wide response takes place as soon as there is a change from the usual mean arterial blood pressure. The baroreceptors identify the changes in both the average blood pressure and the rate of change in pressure with each arterial pulse. At normal resting blood pressures, baroreceptors discharge with each heartbeat and thereby respond rapidly to maintain a stable blood pressure.

Each extrema point observed in the line pressure data 152 is associated with the body reacting to changes in blood pressure away from optimal levels. Therefore, baroreceptors are active during each extrema point to react to the blood pressure changes via the baroreflex. Collecting these events into quantized levels provides a map of how often a patient's baroreflex is stimulated to react to and, typically, reverse the trend of changing blood pressure to keep it at the desired level. This represents a closed loop control system that reacts both to errors and error rate around a set point. Analysis of extrema points represents a fundamental description of the relationship between the physical parts of the cardiovascular system (heart rate, stroke volume, blood vessel resistance, compliance, etc.) and the interaction thereof with the control system (nervous system, brain, baroreceptors, baroreflex, etc.). This interaction and descriptors thereof are necessarily highly individual. Additionally, similarity in overall shape and other more specific indicators may be shared by individuals with similar physiological impairments; therefore, increasing the diagnostic and predictive value of the patient fingerprint(s) 172.

The embodiment(s) detailed hereinabove may be combined in full or in part, with any alternative embodiment(s) described.

INDUSTRIAL APPLICABILITY

The apparatus for non-invasive blood pressure monitoring demonstrates the feasibility of continuous non-invasive blood pressure monitoring without compromising patient experience and without requiring bespoke interfacing to the dialysis machine. Further, the apparatus for non-invasive blood pressure monitoring does not call for additional sensing equipment to be worn by the patient beyond current arm/finger cuff blood pressure monitors already typical during hemodialysis treatments. An approximate mathematical model relating arterial line pressure, blood pump flow rate, and brachial pressure was derived, which predicts a quasi-linear relationship between arm/finger cuff measured blood pressure and corresponding sensor pressure measured in the arterial line proximal the fistula. Interfaces, measurement devices, and a data acquisition apparatus are described herein throughout to support development of the real-time blood pressure estimation model. The results from clinical studies suggest that it is feasible to derive a continuous indication of brachial blood pressure from continuous measurements of arterial and venous line pressures via an empirically based and updated mathematical model trained on intermittently taken blood pressure measurements. More complex and perhaps more accurate parametric models are also contemplated hereby. The methodology and technology described is this disclosure has a practical application in renal units and dialysis clinics. This disclosure also further contemplates iterative learning algorithms to update the mathematical models based upon incoming cuff blood pressure measurements, improved mathematical models to increase estimation accuracy, and predictive models for hypotension.

The disclosed systems and methods can be implemented with a computer system, using, for example, software, hardware, and/or a combination of both, either in a dedicated server, integrated into another entity, or distributed across multiple entities. An exemplary computer system includes a bus or other communication mechanism for communicating information, and a processor coupled with the bus for processing information. The processor may be locally or remotely coupled with the bus. By way of example, the computer system may be implemented with one or more processors. The processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. The computer system also includes a memory, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus for storing information and instructions to be executed by processor.

According to one aspect of the present disclosure, the disclosed system can be implemented using a computer system in response to a processor executing one or more sequences of one or more instructions contained in memory. Such instructions may be read into memory from another machine-readable medium, such as data storage device. Execution of the sequences of instructions contained in main memory causes the processor to perform the process steps described herein. One or more processors in a multi-processing arrangement may also be employed to execute the sequences of instructions contained in memory. In alternative implementations, hard-wired circuitry may be used in place of or in combination with software instructions to implement various implementations of the present disclosure. Thus, implementations of the present disclosure are not limited to any specific combination of hardware circuitry and software. According to one aspect of the disclosure, the disclosed system can be implemented using one or many remote elements in a computer system (e.g., cloud computing), such as a processor that is remote from other elements of the exemplary computer system described above.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Numerous modifications to the present disclosure will be apparent to those skilled in the art in view of the foregoing description. Preferred embodiments of this disclosure are described herein, including the best mode known to the inventors for carrying out the disclosure. It should be understood that the illustrated embodiments are exemplary only and should not be taken as limiting the scope of the disclosure.

What is claimed is:

1. An apparatus for non-invasive blood pressure monitoring, comprising:
    a plurality of pressure sensors;
    a plurality of sensor interfaces coupling the plurality of pressure sensors to at least one blood flow dialysis line disposed exterior from a patient;
    a pump for artificially generating blood flow through the at least one blood flow dialysis line; and
    a processor configured to:
        receive an indication of a blood flow rate of the pump;
        receive pressure sensor measurements from the plurality of pressure sensors,
        and
        execute a learning algorithm to generate a patient blood pressure estimation from the pressure sensor measurements and the blood flow rate, wherein the learning algorithm is trained on comparisons of the patient blood pressure estimation to baseline blood pressure measurements obtained from the patient.

2. The non-invasive blood pressure monitoring apparatus of claim 1, wherein the at least one blood flow dialysis line comprises an arterial dialysis line and a venous dialysis line, and wherein one of the plurality of pressure sensors is coupled to each blood flow dialysis line.

3. The non-invasive blood pressure monitoring apparatus of claim 2, wherein the pressure sensor is coupled to the arterial dialysis line by a Y-connector.

4. The non-invasive blood pressure monitoring apparatus of claim 2, further comprising an arterial dialysis line air trap and a venous dialysis line air trap, respectively, coupling the corresponding pressure sensors to each of the arterial dialysis line and the venous dialysis line.

5. The non-invasive blood pressure monitoring apparatus of claim 4, wherein each air trap comprises an impermeable membrane and a filter.

6. The non-invasive blood pressure monitoring apparatus of claim 1, wherein the processor further executes the learning algorithm to estimate the blood flow rate of the pump.

7. The non-invasive blood pressure monitoring apparatus of claim 1, wherein the processor generates the patient blood pressure estimation over a period defined by a hemodialysis treatment session.

8. The non-invasive blood pressure monitoring apparatus of claim 1, wherein the processor generates the patient blood pressure estimation over a period defined by a plurality of hemodialysis treatment sessions.

9. A system for reconstructing blood pressure information, comprising:
    a learning algorithm module;
    a plurality of pressure sensors disposed within arterial and venous dialysis lines;
    a flow rate sensor for measuring a blood flow rate through a pump;
    and
    a processor and memory, wherein the processor applies a Fourier transform to line pressures observed from the plurality of pressure sensors;
    wherein the processor combines a decomposed function of the line pressures with the measured blood flow rate to model a blood pressure;
    wherein the learning algorithm module is trained on comparisons of the modeled blood pressure to a baseline blood pressure.

10. The system for reconstructing blood pressure information of claim 9, wherein the learning algorithm module learns physical dynamics of pressure waveforms in the arterial and venous dialysis lines.

11. The system for reconstructing blood pressure information of claim 10, wherein the learning algorithm module models a relationship between pump speed and the pressure waveforms in the arterial and venous dialysis lines.

12. The system for reconstructing blood pressure information of claim 11, wherein the learning algorithm module is trained on mean and amplitude data of the arterial and venous dialysis lines.

13. The system for reconstructing blood pressure information of claim 12, wherein the baseline blood pressure is measured by a blood pressure cuff.

14. The system for reconstructing blood pressure information of claim 13, wherein the learning algorithm module accounts for change in diameter of the arterial and venous dialysis lines and diameter of a pump dialysis line.

15. The system for reconstructing blood pressure information of claim 14, wherein the learning algorithm module accounts for change in placement of the pressure sensors along the arterial and venous dialysis lines and the pump dialysis line.

16. A method of generating blood pressure estimations, comprising:
    connecting arterial and venous blood lines to a fistula disposed within a patient;
    arranging at least one pressure sensor to detect pulsatile pressure for each of the arterial and venous blood lines exterior to the fistula;
    coupling the arterial and venous blood lines to a peristaltic roller pump;
    accepting as inputs by a learning algorithm: arterial line pressure, venous line pressure, and pump speed;
    applying, by the learning algorithm, a Fourier transform to the inputs to generate an expected blood pressure of the patient;
    measuring baseline blood pressures for the patient; and
    training the learning algorithm by comparing the generated expected blood pressure of the patient to the baseline blood pressures of the patient.

17. The method of generating blood pressure estimations of claim 16, further comprising:
    forming an arterial air trap;
    forming a venous air trap; and
    connecting the at least one pressure sensor for each of the arterial and venous blood lines to the corresponding air trap.

18. The method of generating blood pressure estimations of claim 17, further comprising:
    inputting dimensions of the pump and blood lines to the learning algorithm.

19. The method of generating blood pressure estimations of claim 16, wherein the baseline blood pressures are measured with a blood pressure cuff.

* * * * *